(12) United States Patent
Davidson

(10) Patent No.: US 10,076,399 B2
(45) Date of Patent: Sep. 18, 2018

(54) ENDOVASCULAR DEVICE ENGAGEMENT

(71) Applicant: Covidien LP, Mansfield, MA (US)

(72) Inventor: James A. Davidson, San Juan Capistrano, CA (US)

(73) Assignee: COVIDIEN LP, Mansfield, MA (US)

( * ) Notice: Subject to any disclaimer, the term of this patent is extended or adjusted under 35 U.S.C. 154(b) by 750 days.

(21) Appl. No.: 14/026,302

(22) Filed: Sep. 13, 2013

(65) Prior Publication Data

US 2015/0080937 A1 Mar. 19, 2015

(51) Int. Cl.
| | | |
|---|---|---|
| *A61M 29/00* | (2006.01) | |
| *A61F 2/01* | (2006.01) | |
| *A61B 17/221* | (2006.01) | |
| *A61B 17/00* | (2006.01) | |
| *A61B 17/22* | (2006.01) | |
| *A61B 90/00* | (2016.01) | |

(52) U.S. Cl.
CPC ............. *A61F 2/01* (2013.01); *A61B 17/221* (2013.01); *A61B 2017/00867* (2013.01); *A61B 2017/00893* (2013.01); *A61B 2017/2215* (2013.01); *A61B 2017/22034* (2013.01); *A61B 2090/3966* (2016.02); *A61F 2002/011* (2013.01); *A61F 2002/016* (2013.01)

(58) Field of Classification Search
CPC ...... A61F 2/01; A61F 2/88; A61F 2/90; A61F 2002/18; A61F 2250/0029; A61F 2250/0048; A61B 17/3207
USPC ........................................................ 606/200
See application file for complete search history.

(56) References Cited

U.S. PATENT DOCUMENTS

| 3,996,938 A | 12/1976 | Clark, III |
| 4,046,150 A | 9/1977 | Schwartz et al. |
| 4,299,255 A | 11/1981 | Miller |

(Continued)

FOREIGN PATENT DOCUMENTS

| BR | 9604566 A | 9/1998 |
| CA | 2389374 A1 | 5/2001 |

(Continued)

OTHER PUBLICATIONS

US 6,056,761, 05/2000, Gia (withdrawn)

(Continued)

*Primary Examiner* — Kathleen Holwerda
*Assistant Examiner* — Christina Lauer
(74) *Attorney, Agent, or Firm* — Fortem IP LLP; Matthew Lincicum

(57) ABSTRACT

A medical device, configured to perform an endovascular therapy, e.g., thrombectomy, can comprise an elongate manipulation member and an intervention member. The intervention member can comprise a proximal end portion and a mesh. The proximal end portion can be coupled with the distal end portion of the elongate manipulation member. The mesh can have a plurality of cells and, be compressible to a collapsed configuration for delivery to an endovascular treatment site through a catheter, and be self-expandable from the collapsed configuration to an expanded configuration. At least a portion of the mesh, from a first location to a second location along the mesh, can be configured such that an amount of cell deformation in response to longitudinally directed tensile forces decreases by less than 5% or increases in a distal direction along the portion of the mesh.

31 Claims, 17 Drawing Sheets

(56) References Cited

U.S. PATENT DOCUMENTS

| | | |
|---|---|---|
| 4,347,846 A | 9/1982 | Dormia |
| 4,611,594 A | 9/1986 | Grayhack et al. |
| 4,612,931 A | 9/1986 | Dormia |
| 4,650,466 A | 3/1987 | Luther |
| 4,655,771 A | 4/1987 | Wallsten |
| 4,733,665 A | 3/1988 | Palmaz |
| 4,739,762 A | 4/1988 | Palmaz |
| 4,793,348 A | 12/1988 | Palmaz |
| 4,890,611 A | 1/1990 | Monfort et al. |
| 5,071,407 A | 12/1991 | Termin et al. |
| 5,100,423 A | 3/1992 | Fearnot |
| 5,102,417 A | 4/1992 | Palmaz |
| 5,147,370 A * | 9/1992 | McNamara ............... A61F 2/88 606/108 |
| 5,190,058 A | 3/1993 | Jones et al. |
| 5,192,286 A | 3/1993 | Phan et al. |
| 5,195,984 A | 3/1993 | Schatz |
| 5,197,978 A | 3/1993 | Hess |
| 5,217,484 A | 6/1993 | Marks |
| 5,222,971 A | 6/1993 | Willard et al. |
| 5,330,482 A | 7/1994 | Gibbs et al. |
| 5,354,295 A | 10/1994 | Guglielmi et al. |
| 5,411,549 A | 5/1995 | Peters |
| 5,423,829 A | 6/1995 | Pham et al. |
| 5,456,667 A | 10/1995 | Ham et al. |
| 5,490,859 A | 2/1996 | Mische et al. |
| 5,496,330 A | 3/1996 | Bates et al. |
| 5,501,694 A | 3/1996 | Ressemann et al. |
| 5,527,326 A | 6/1996 | Hermann et al. |
| 5,540,680 A | 7/1996 | Guglielmi et al. |
| 5,540,707 A | 7/1996 | Ressemann et al. |
| 5,569,245 A | 10/1996 | Guglielmi et al. |
| 5,571,122 A | 11/1996 | Kelly et al. |
| 5,573,520 A | 11/1996 | Schwartz et al. |
| 5,624,449 A | 4/1997 | Pham et al. |
| 5,669,933 A | 9/1997 | Simon et al. |
| 5,690,667 A | 11/1997 | Gia |
| 5,695,519 A | 12/1997 | Summers et al. |
| 5,720,764 A | 2/1998 | Naderlinger |
| 5,743,905 A | 4/1998 | Eder et al. |
| 5,749,883 A | 5/1998 | Halpern |
| 5,759,192 A | 6/1998 | Saunders |
| 5,769,882 A | 6/1998 | Fogarty et al. |
| 5,792,145 A | 8/1998 | Bates et al. |
| 5,792,157 A | 8/1998 | Mische et al. |
| 5,800,454 A | 9/1998 | Jacobsen et al. |
| 5,800,520 A | 9/1998 | Fogarty et al. |
| 5,800,525 A | 9/1998 | Bachinski et al. |
| 5,814,064 A | 9/1998 | Daniel et al. |
| 5,824,037 A | 10/1998 | Fogarty et al. |
| 5,827,304 A | 10/1998 | Hart |
| 5,836,868 A | 11/1998 | Ressemann et al. |
| 5,848,964 A | 12/1998 | Samuels |
| 5,851,206 A | 12/1998 | Guglielmi et al. |
| 5,855,578 A | 1/1999 | Guglielmi et al. |
| 5,882,329 A | 3/1999 | Patterson et al. |
| 5,891,128 A | 4/1999 | Gia et al. |
| 5,895,385 A | 4/1999 | Guglielmi et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,717 A | 6/1999 | Jacobsen et al. |
| 5,911,734 A | 6/1999 | Tsugita et al. |
| 5,913,895 A | 6/1999 | Burpee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,061 A | 7/1999 | Ogi et al. |
| 5,928,226 A | 7/1999 | Guglielmi et al. |
| 5,935,139 A | 8/1999 | Bates |
| 5,941,869 A | 8/1999 | Patterson et al. |
| 5,944,714 A | 8/1999 | Guglielmi et al. |
| 5,947,962 A | 9/1999 | Guglielmi et al. |
| 5,947,995 A | 9/1999 | Samuels |
| 5,948,016 A | 9/1999 | Jang |
| 5,954,743 A | 9/1999 | Jang |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |
| 5,980,514 A | 11/1999 | Kupiecki et al. |
| 5,984,929 A | 11/1999 | Bashiri et al. |
| 6,010,498 A | 1/2000 | Guglielmi |
| 6,013,093 A | 1/2000 | Nott et al. |
| 6,063,100 A | 5/2000 | Diaz et al. |
| 6,063,111 A | 5/2000 | Hieshima et al. |
| 6,066,149 A | 5/2000 | Samson et al. |
| 6,066,158 A | 5/2000 | Engelson et al. |
| 6,077,260 A | 6/2000 | Wheelock et al. |
| 6,083,220 A | 7/2000 | Guglielmi et al. |
| 6,096,034 A | 8/2000 | Kupiecki et al. |
| 6,096,053 A | 8/2000 | Bates |
| 6,099,549 A | 8/2000 | Bosma et al. |
| 6,110,198 A | 8/2000 | Fogarty et al. |
| 6,118,001 A | 9/2000 | Owen et al. |
| 6,123,714 A | 9/2000 | Gia et al. |
| 6,129,755 A | 10/2000 | Mathis et al. |
| 6,146,396 A | 11/2000 | Konya et al. |
| 6,156,061 A | 12/2000 | Wallace et al. |
| 6,165,178 A | 12/2000 | Bashiri et al. |
| 6,165,213 A | 12/2000 | Goicoechea et al. |
| 6,168,592 B1 | 1/2001 | Kupiecki et al. |
| 6,168,603 B1 | 1/2001 | Leslie et al. |
| 6,179,857 B1 | 1/2001 | Diaz et al. |
| 6,187,017 B1 | 2/2001 | Gregory, Jr. |
| 6,190,394 B1 | 2/2001 | Lind et al. |
| 6,193,745 B1 | 2/2001 | Fogarty et al. |
| 6,203,552 B1 | 3/2001 | Bagley et al. |
| 6,214,025 B1 | 4/2001 | Thistle et al. |
| 6,238,412 B1 | 5/2001 | Dubrul et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,686 B1 | 7/2001 | Rieu et al. |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,306,141 B1 | 10/2001 | Jervis |
| 6,312,463 B1 | 11/2001 | Rourke et al. |
| 6,325,815 B1 | 12/2001 | Kusleika et al. |
| 6,336,934 B1 | 1/2002 | Gilson et al. |
| 6,344,041 B1 | 2/2002 | Kupiecki et al. |
| 6,361,558 B1 | 3/2002 | Hieshima et al. |
| 6,371,969 B1 | 4/2002 | Tsugita et al. |
| 6,379,329 B1 | 4/2002 | Naglreiter et al. |
| 6,383,205 B1 | 5/2002 | Samson et al. |
| 6,402,771 B1 | 6/2002 | Palmer et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,443,972 B1 | 9/2002 | Bosma et al. |
| 6,458,139 B1 | 10/2002 | Palmer et al. |
| 6,468,266 B1 | 10/2002 | Bashiri et al. |
| 6,485,524 B2 | 11/2002 | Strecker |
| 6,491,719 B1 | 12/2002 | Fogarty et al. |
| 6,500,182 B2 | 12/2002 | Foster |
| 6,514,273 B1 | 2/2003 | Voss et al. |
| 6,520,968 B2 | 2/2003 | Bates et al. |
| 6,530,935 B2 | 3/2003 | Wensel et al. |
| 6,533,811 B1 | 3/2003 | Ryan et al. |
| 6,551,342 B1 | 4/2003 | Shen et al. |
| 6,554,849 B1 | 4/2003 | Jones et al. |
| 6,572,648 B1 | 6/2003 | Klumb et al. |
| 6,575,997 B1 | 6/2003 | Palmer et al. |
| 6,589,230 B2 | 7/2003 | Gia et al. |
| 6,589,236 B2 | 7/2003 | Wheelock et al. |
| 6,592,607 B1 | 7/2003 | Palmer et al. |
| 6,620,152 B2 | 9/2003 | Guglielmi |
| 6,641,590 B1 | 11/2003 | Palmer et al. |

(56) References Cited

U.S. PATENT DOCUMENTS

| | | | |
|---|---|---|---|
| 6,645,224 B2 | 11/2003 | Gilson et al. | |
| 6,652,548 B2 | 11/2003 | Evans et al. | |
| 6,656,214 B1 | 12/2003 | Fogarty et al. | |
| 6,660,014 B2 | 12/2003 | Demarais et al. | |
| 6,660,021 B1 | 12/2003 | Palmer et al. | |
| 6,663,650 B2 | 12/2003 | Sepetka et al. | |
| 6,673,106 B2 | 1/2004 | Mitelberg et al. | |
| 6,679,893 B1 | 1/2004 | Tran | |
| 6,692,508 B2 | 2/2004 | Wensel et al. | |
| 6,702,782 B2 | 3/2004 | Miller et al. | |
| 6,716,238 B2 | 4/2004 | Elliott | |
| 6,723,108 B1 | 4/2004 | Jones et al. | |
| 6,743,236 B2 | 6/2004 | Barry et al. | |
| 6,811,560 B2 | 11/2004 | Jones et al. | |
| 6,818,013 B2 | 11/2004 | Mitelberg et al. | |
| 6,833,002 B2 | 12/2004 | Stack et al. | |
| 6,833,003 B2 | 12/2004 | Jones et al. | |
| 6,878,151 B2 | 4/2005 | Carrison et al. | |
| 6,887,268 B2 | 5/2005 | Butaric et al. | |
| 6,893,413 B2 | 5/2005 | Martin | |
| 6,913,612 B2 | 7/2005 | Palmer et al. | |
| 6,921,414 B2 | 7/2005 | Klumb et al. | |
| 6,945,977 B2 | 9/2005 | Demarais et al. | |
| 6,953,468 B2 | 10/2005 | Jones et al. | |
| 6,955,685 B2 | 10/2005 | Escamilla et al. | |
| 6,960,227 B2 | 11/2005 | Jones et al. | |
| 6,960,228 B2 | 11/2005 | Mitelberg et al. | |
| 6,974,473 B2 | 12/2005 | Barclay et al. | |
| 6,989,020 B2 | 1/2006 | Jones et al. | |
| 7,001,422 B2 | 2/2006 | Escamilla et al. | |
| 7,004,954 B1 | 2/2006 | Voss et al. | |
| 7,004,956 B2 | 2/2006 | Palmer et al. | |
| 7,037,331 B2 | 5/2006 | Mitelberg et al. | |
| 7,041,116 B2 | 5/2006 | Goto et al. | |
| 7,052,500 B2 | 5/2006 | Bashiri et al. | |
| 7,058,456 B2 | 6/2006 | Pierce | |
| 7,101,380 B2 | 9/2006 | Khachin et al. | |
| 7,128,073 B1 | 10/2006 | van der Burg et al. | |
| 7,147,659 B2 | 12/2006 | Jones | |
| 7,156,871 B2 | 1/2007 | Jones et al. | |
| 7,179,273 B1 | 2/2007 | Palmer et al. | |
| 7,179,276 B2 | 2/2007 | Barry et al. | |
| 7,182,774 B2 | 2/2007 | Barry et al. | |
| 7,195,648 B2 | 3/2007 | Jones et al. | |
| 7,201,769 B2 | 4/2007 | Jones et al. | |
| 7,232,432 B2 | 6/2007 | Fulton, III et al. | |
| 7,264,628 B2 | 9/2007 | Jones et al. | |
| 7,270,674 B2 | 9/2007 | Jones et al. | |
| 7,285,126 B2 | 10/2007 | Sepetka et al. | |
| 7,294,123 B2 | 11/2007 | Jones et al. | |
| 7,300,458 B2 | 11/2007 | Henkes et al. | |
| 7,306,622 B2 | 12/2007 | Jones et al. | |
| 7,309,351 B2 | 12/2007 | Escamilla et al. | |
| 7,311,726 B2 | 12/2007 | Mitelberg et al. | |
| 7,323,000 B2 | 1/2008 | Monstdt et al. | |
| 7,344,550 B2 | 3/2008 | Carrison et al. | |
| 7,344,558 B2 | 3/2008 | Lorenzo et al. | |
| 7,357,809 B2 | 4/2008 | Jones et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,481,821 B2 | 1/2009 | Fogarty et al. | |
| 7,485,122 B2 | 2/2009 | Teoh | |
| 7,510,565 B2 | 3/2009 | Gilson et al. | |
| 7,517,352 B2 | 4/2009 | Evans et al. | |
| 7,524,319 B2 | 4/2009 | Dubrul | |
| 7,534,252 B2 | 5/2009 | Sepetka et al. | |
| 7,553,314 B2 | 6/2009 | Khachin et al. | |
| 7,553,321 B2 | 6/2009 | Litzenberg et al. | |
| 7,582,101 B2 | 9/2009 | Jones et al. | |
| 7,582,111 B2 * | 9/2009 | Krolik | A61F 2/91 623/1.15 |
| 7,780,694 B2 | 8/2010 | Palmer et al. | |
| 8,025,693 B2 * | 9/2011 | Quigley | A61F 2/07 623/1.13 |
| 8,197,493 B2 | 6/2012 | Ferrera et al. | |
| 8,357,179 B2 | 1/2013 | Grandfield et al. | |
| 8,540,763 B2 | 9/2013 | Jones et al. | |
| 8,623,068 B2 * | 1/2014 | Shanley | A61F 2/91 623/1.15 |
| 9,072,537 B2 * | 7/2015 | Grandfield | A61B 17/221 |
| 2001/0003801 A1 | 6/2001 | Strecker | |
| 2001/0041899 A1 | 11/2001 | Foster | |
| 2001/0044649 A1 | 11/2001 | Vallana et al. | |
| 2001/0053929 A1 | 12/2001 | Vonesh et al. | |
| 2002/0193868 A1 | 12/2002 | Mitelberg et al. | |
| 2003/0153944 A1 | 8/2003 | Phung et al. | |
| 2004/0010308 A1 | 1/2004 | Zafrir-Pachter et al. | |
| 2004/0059407 A1 | 3/2004 | Escamilla et al. | |
| 2004/0078050 A1 | 4/2004 | Monstadt et al. | |
| 2004/0098025 A1 | 5/2004 | Sepetka et al. | |
| 2005/0021125 A1 | 1/2005 | Stack et al. | |
| 2005/0033348 A1 | 2/2005 | Sepetka et al. | |
| 2005/0165441 A1 | 7/2005 | McGuckin et al. | |
| 2005/0209678 A1 | 9/2005 | Henkes et al. | |
| 2005/0222676 A1 | 10/2005 | Shanley et al. | |
| 2006/0085065 A1 | 4/2006 | Krause et al. | |
| 2006/0195118 A1 | 8/2006 | Richardson | |
| 2006/0224179 A1 | 10/2006 | Kucharczyk et al. | |
| 2007/0179513 A1 | 8/2007 | Deutsch | |
| 2007/0185501 A1 | 8/2007 | Martin et al. | |
| 2007/0198029 A1 | 8/2007 | Martin et al. | |
| 2007/0208367 A1 | 9/2007 | Fiorella et al. | |
| 2007/0208371 A1 | 9/2007 | French et al. | |
| 2007/0225749 A1 | 9/2007 | Martin et al. | |
| 2007/0266542 A1 | 11/2007 | Melsheimer | |
| 2007/0288038 A1 | 12/2007 | Bimbo | |
| 2008/0082107 A1 | 4/2008 | Miller et al. | |
| 2008/0119888 A1 | 5/2008 | Huffmaster | |
| 2008/0125855 A1 | 5/2008 | Henkes et al. | |
| 2008/0183185 A1 | 7/2008 | Miller et al. | |
| 2008/0183198 A1 | 7/2008 | Sepetka et al. | |
| 2008/0188865 A1 | 8/2008 | Miller et al. | |
| 2008/0269774 A1 | 10/2008 | Garcia et al. | |
| 2009/0069828 A1 | 3/2009 | Martin et al. | |
| 2009/0163851 A1 | 6/2009 | Holloway et al. | |
| 2009/0275974 A1 | 11/2009 | Marchand et al. | |
| 2009/0299393 A1 | 12/2009 | Martin et al. | |
| 2010/0004735 A1 * | 1/2010 | Yang | A61F 2/91 623/1.16 |
| 2010/0174309 A1 | 7/2010 | Fulkerson et al. | |
| 2011/0060212 A1 | 3/2011 | Slee et al. | |
| 2011/0160763 A1 * | 6/2011 | Ferrera | A61B 17/221 606/200 |
| 2012/0083868 A1 | 4/2012 | Shrivastava et al. | |
| 2012/0209311 A1 | 8/2012 | Grandfield et al. | |
| 2013/0030460 A1 * | 1/2013 | Marks | A61B 17/221 606/200 |
| 2013/0158592 A1 * | 6/2013 | Porter | A61B 17/221 606/200 |

FOREIGN PATENT DOCUMENTS

| | | |
|---|---|---|
| CN | 102973332 A | 3/2013 |
| CN | 103153214 A | 6/2013 |
| DE | 2804058 A1 | 8/1978 |
| DE | 2821048 B1 | 11/1979 |
| DE | 8435489 U1 | 8/1986 |
| DE | 19703482 A1 | 8/1998 |
| DE | 10010840 A1 | 9/2001 |
| EP | 201466 A2 | 11/1986 |
| EP | 484468 A1 | 5/1992 |
| EP | 629125 A1 | 12/1994 |
| EP | 707830 A1 | 4/1996 |
| EP | 719522 A1 | 7/1996 |
| EP | 726745 A1 | 8/1996 |
| EP | 737450 A1 | 10/1996 |
| EP | 739606 A1 | 10/1996 |
| EP | 750886 A1 | 1/1997 |
| EP | 752236 A1 | 1/1997 |
| EP | 800790 A2 | 10/1997 |

(56) References Cited

FOREIGN PATENT DOCUMENTS

| | | |
|---|---|---|
| EP | 803230 A2 | 10/1997 |
| EP | 804904 A1 | 11/1997 |
| EP | 804905 A1 | 11/1997 |
| EP | 804906 A2 | 11/1997 |
| EP | 807410 A2 | 11/1997 |
| EP | 820729 A1 | 1/1998 |
| EP | 826341 A1 | 3/1998 |
| EP | 826342 A1 | 3/1998 |
| EP | 832606 A1 | 4/1998 |
| EP | 861634 A2 | 9/1998 |
| EP | 914803 A1 | 5/1999 |
| EP | 964659 A1 | 12/1999 |
| EP | 1005837 A2 | 6/2000 |
| EP | 1009295 A1 | 6/2000 |
| EP | 1009296 A1 | 6/2000 |
| EP | 1225844 A2 | 7/2002 |
| EP | 1266639 A2 | 12/2002 |
| EP | 1266640 A2 | 12/2002 |
| EP | 1323385 A2 | 7/2003 |
| EP | 1329196 A1 | 7/2003 |
| EP | 1351626 A2 | 10/2003 |
| EP | 1366720 A1 | 12/2003 |
| EP | 1400219 A1 | 3/2004 |
| EP | 1867290 | 12/2007 |
| EP | 2959853 A1 | 12/2015 |
| FR | 2343488 A1 | 10/1977 |
| GB | 2020557 A | 11/1979 |
| JP | 2-95359 A | 4/1990 |
| JP | 02255157 A | 10/1990 |
| JP | 6-246004 | 9/1994 |
| JP | 8-033719 A | 2/1996 |
| JP | 2975584 B2 | 11/1999 |
| JP | 2001-190686 A | 7/2001 |
| JP | 2001178830 A | 7/2001 |
| WO | WO-96/017634 A2 | 6/1996 |
| WO | WO-96/028116 A1 | 9/1996 |
| WO | WO-97/04711 A1 | 2/1997 |
| WO | WO-98/25656 A3 | 10/1998 |
| WO | WO-98/055175 A1 | 12/1998 |
| WO | WO-99/016382 A2 | 4/1999 |
| WO | WO-99/023976 A1 | 5/1999 |
| WO | WO-99/025252 A1 | 5/1999 |
| WO | WO-99/029264 A1 | 6/1999 |
| WO | WO-99/044542 A2 | 9/1999 |
| WO | WO-99/048429 A1 | 9/1999 |
| WO | WO-99/048440 A1 | 9/1999 |
| WO | WO-00/012166 A1 | 3/2000 |
| WO | WO-00/59405 A1 | 10/2000 |
| WO | WO-01/032099 A2 | 5/2001 |
| WO | WO-01/045566 A1 | 6/2001 |
| WO | WO-01/072240 A1 | 10/2001 |
| WO | WO-01/93780 A2 | 12/2001 |
| WO | WO-02/054980 A2 | 7/2002 |
| WO | WO-2004008991 A1 | 1/2004 |
| WO | WO-2008063156 A2 | 5/2008 |
| WO | WO-2009/105710 A1 | 8/2009 |
| WO | WO-2012/085073 A2 | 6/2012 |
| WO | WO-2012/120490 A2 | 9/2012 |

OTHER PUBLICATIONS

Henkes, H., et al., "A Novel Microcatheter-Delivered, Highly-Flexible and Fully-Retrievable Stent, Specifically Designed for Intracranial Use", Interventional Neuroradiolog, vol. 9, pp. 391-393.

* cited by examiner

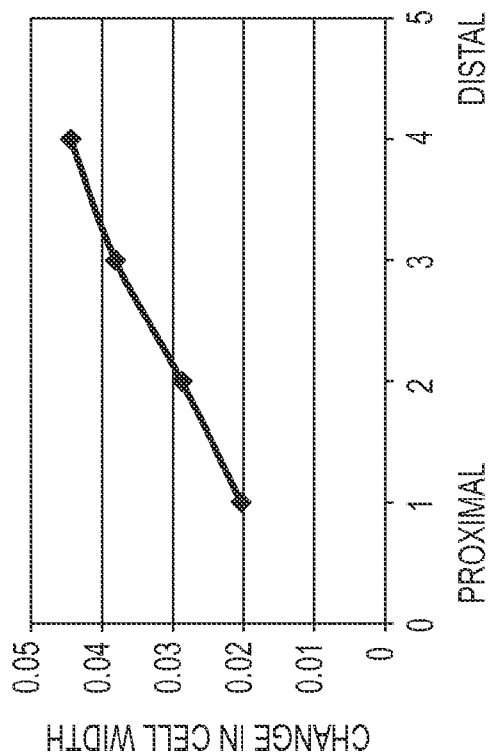
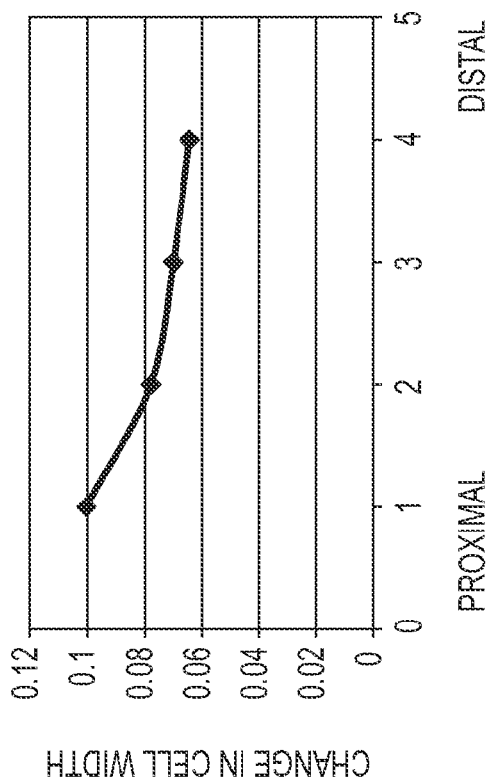
FIG.6B
FIG.6A

ENDOVASCULAR DEVICE ENGAGEMENT

BACKGROUND

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

An aspect of at least some of the embodiments disclosed herein involves the recognition that the location and longitudinal extent of thrombus engagement by a mechanical thrombus-retrieval device can affect the likelihood of successfully capturing the engaged thrombus, and that the likelihood of successful thrombus capture and retrieval can be improved by increasing a longitudinal extent of substantially even thrombus engagement, distally shifting the region of thrombus engagement, or both. When a thrombus is primarily engaged along a portion of the thrombus near its proximal end, and particularly when a longitudinal extent of substantially even thrombus engagement is small, the thrombus may be more likely to fragment, become released from the retrieval device, or both.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 8, 22, 32, 40, 47, 56, 65, or 69. The other clauses can be presented in a similar manner.

1. A medical device configured to perform an endovascular therapy, the device comprising:
an elongate manipulation member comprising a distal end portion; and
an intervention member comprising a proximal end portion and a mesh, the proximal end portion being coupled with the distal end portion of the elongate manipulation member, the mesh having a proximal mesh end, a distal mesh end, and a mesh length from the proximal end to the distal end, the mesh having a plurality of cells and being compressible to a collapsed configuration for delivery to an endovascular treatment site through a catheter and being self-expandable from the collapsed configuration to an expanded configuration, and wherein at least a portion of the mesh, from a first location to a second location along the mesh, is configured such that an amount of cell deformation in response to longitudinally directed tensile forces decreases by less than 5% or increases in a distal direction along the portion of the mesh, the first and second locations being longitudinally separated by a distance that is more than half of the mesh length.

2. The medical device of Clause 1, wherein the portion of the mesh, from the first location to the second location along the mesh, is configured such that the amount of cell deformation in response to longitudinally directed tensile forces does not decrease in a distal direction along the portion of the mesh.

3. The medical device of Clause 1, wherein the portion of the mesh, from the first location to the second location along the mesh, is configured such that the amount of cell deformation in response to longitudinally directed tensile forces increases in a distal direction along the portion of the mesh.

4. The medical device of Clause 1, wherein the first and second locations are longitudinally separated by a distance that is at least two thirds of the mesh length.

5. The medical device of Clause 1, wherein the first and second locations are longitudinally separated by a distance that is at least three quarters of the mesh length.

6. The medical device of Clause 1, wherein the first and second locations are longitudinally separated by a distance that is at least 90% of the mesh length.

7. The medical device of Clause 1, wherein the mesh is generally cylindrical in the absence of external forces.

8. A medical device configured to perform an endovascular therapy, the device comprising:
an elongate manipulation member comprising a distal end portion; and
an intervention member comprising a proximal end portion and a plurality of cells forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, and wherein, from a first location to a second location along the mesh, each cell distally adjacent to another cell, in a longitudinal row of cells, has a larger interior bounded area than has the another cell, the first and second locations being longitudinally separated by a distance that is more than half of the mesh length.

9. The medical device of Clause 8, wherein the first and second locations are longitudinally separated by a distance that is at least two thirds of the mesh length.

10. The medical device of Clause 8, wherein the first and second locations are longitudinally separated by a distance that is at least three quarters of the mesh length.

11. The medical device of Clause 8, wherein the first and second locations are longitudinally separated by a distance that is at least 90% of the mesh length.

12. The medical device of Clause 8, wherein the longitudinal row of cells comprises at least three cells.

13. The medical device of Clause 8, wherein the first location is at the proximal mesh end.

14. The medical device of Clause 8, wherein the first location is distal to a proximal-most cell.

15. The medical device of Clause 8, wherein the second location is at the distal mesh end.

16. The medical device of Clause 8, wherein the mesh is cylindrical in the absence of external forces.

17. The medical device of Clause 8, wherein the elongate manipulation member has a length between a proximal end and the distal end that is sufficient to permit manipulation of the intervention member within the cerebral vasculature of a patient's body from a location outside the body.

18. The medical device of Clause 8, wherein the mesh is formed by laser cutting one of a tube or a sheet.

19. The medical device of Clause 8, wherein the mesh forms a generally tubular structure.

20. The medical device of Clause 8, wherein the mesh further comprises a first lateral edge extending between the proximal mesh end and the distal mesh end, and a second lateral edge opposite the first lateral edge, the second lateral edge extending between the proximal mesh end and the distal mesh end; wherein the first and second lateral edges are overlapped in a coiled configuration about the longitudinal axis when the mesh is in the collapsed configuration.

21. The medical device of Clause 8, wherein the tube has an open proximal end and an open distal end.

22. A medical device configured to perform an endovascular therapy, the device comprising:
an elongate manipulation member comprising a distal end portion; and
an intervention member comprising a proximal end portion and a plurality of cells forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, and wherein, in a longitudinal row of at least three cells, each cell distally adjacent to another cell has a larger proximal inscribed strut angle between first and second struts (i) bounding a proximal portion of the cell and (ii) diverging in a distal direction, than has the another cell.

23. The medical device of Clause 22, wherein the first and second struts comprises a straight portion and a curved portion, and the inscribed strut angle is measured between the straight portions of the first and second struts.

24. The medical device of Clause 22, wherein the inscribe strut angle is measured between straight reference lines that join strut intersection points at each end of the first and second struts.

25. The medical device of Clause 22, wherein, for each cell, the first strut has a length equal to that of the second strut.

26. The medical device of Clause 22, wherein the first struts of all cells between the first and second locations have the substantially equal lengths.

27. The medical device of Clause 22, wherein the longitudinal row extends from a first location to a second location along the mesh, the first and second locations being longitudinally separated by a distance that is more than half of the mesh length.

28. The medical device of Clause 27, wherein the first and second locations are longitudinally separated by a distance that is at least two thirds of the mesh length.

29. The medical device of Clause 27, wherein the first and second locations are longitudinally separated by a distance that is at least three quarters of the mesh length.

30. The medical device of Clause 27, wherein the first and second locations are longitudinally separated by a distance that is at least 90% of the mesh length.

31. The medical device of Clause 22, wherein the mesh is cylindrical in the absence of external forces.

32. A medical device configured to perform an endovascular therapy, the device comprising:
an elongate manipulation member comprising a distal end portion; and
an intervention member comprising a proximal end portion and a plurality of cells forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, and wherein, from a first location to a second location along the mesh, each cell distally adjacent to another cell, in a longitudinal row of cells, has a larger maximum cell width than has the another cell, the first and second locations being longitudinally separated by a distance that is more than half of the mesh length.

33. The medical device of Clause 32, wherein each cell comprises first and second struts (i) bounding a proximal portion of the cell and (ii) diverging in a distal direction, and third and fourth struts (i) bounding a distal portion of the cell and (ii) converging in a distal direction, the maximum cell width is measured from an intersection of the first strut and the third strut to an intersection of the second strut with the fourth strut.

34. The medical device of Clause 32, wherein, for each cell, the first strut has a length equal to that of the second strut.

35. The medical device of Clause 32, wherein the first struts of all cell between the first and second locations have the substantially equal lengths.

36. The medical device of Clause 32, wherein the first and second locations are longitudinally separated by a distance that is at least two thirds of the mesh length.

37. The medical device of Clause 32, wherein the first and second locations are longitudinally separated by a distance that is at least three quarters of the mesh length.

38. The medical device of Clause 32, wherein the first and second locations are longitudinally separated by a distance that is at least 90% of the mesh length.

39. The medical device of Clause 32, wherein the mesh is cylindrical in the absence of external forces.

40. A medical device configured to perform an endovascular therapy, the device comprising:
an elongate manipulation member comprising a distal end portion; and
an intervention member comprising a proximal end portion and a plurality of sinuous members, the sinuous members connected to form a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, each sinuous member comprising a plurality of oscillations, and wherein, from a first location to a second location along the mesh, an amplitude of the oscillations of each sinuous member increases in a distal direction, the first and second locations being longitudinally separated by a distance that is more than half of the mesh length.

41. The medical device of Clause 40, wherein the amplitude of the oscillations increases distally at a constant rate per unit length.

42. The medical device of Clause 40, wherein the frequency of the oscillations increases distally.

43. The medical device of Clause 40, wherein the first and second locations are longitudinally separated by a distance that is at least two thirds of the mesh length.

44. The medical device of Clause 40, wherein the first and second locations are longitudinally separated by a distance that is at least three quarters of the mesh length.

45. The medical device of Clause 40, wherein the first and second locations are longitudinally separated by a distance that is at least 90% of the mesh length.

46. The medical device of Clause 40, wherein the mesh is cylindrical in the absence of external forces.

47. A medical device configured to perform an endovascular therapy, the device comprising:
   an elongate manipulation member comprising a distal end portion; and
   an intervention member comprising a proximal end portion and a plurality of struts forming a mesh, the proximal end portion being coupled with the distal end portion of the elongate manipulation member, the mesh comprising a plurality of generally longitudinally arranged rows of cells and having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, a reference line for each row of at least three cells, each reference line passing through all intersections of adjacent cells in the corresponding row, and adjacent references lines diverging distally.

48. The medical device of Clause 47, wherein, between the first and second locations, all of the reference lines continuously diverge from each adjacent reference line.

49. The medical device of Clause 47, wherein at least one references line is straight.

50. The medical device of Clause 47, wherein all of the references line are straight.

51. The medical device of Clause 47, wherein each row extends from a first location to a second location along the mesh, the first and second locations being longitudinally separated by a distance that is more than half of the mesh length.

52. The medical device of Clause 51, wherein the first and second locations are longitudinally separated by a distance that is at least two thirds of the mesh length.

53. The medical device of Clause 51, wherein the first and second locations are longitudinally separated by a distance that is at least three quarters of the mesh length.

54. The medical device of Clause 51, wherein the first and second locations are longitudinally separated by a distance that is at least 90% of the mesh length.

55. The medical device of Clause 47, wherein the mesh is cylindrical in the absence of external forces.

56. A medical device configured to perform an endovascular therapy, the device comprising:
   an elongate manipulation member comprising a distal end portion; and
   an intervention member comprising a proximal end portion and a plurality of struts forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, and wherein, from a first location to a second location along the mesh, each cell distally adjacent to another cell has a strut that is more deflectable than a strut of the another cell, the first and second locations being longitudinally separated by a distance that is more than half of the mesh length.

57. The medical device of Clause 56, wherein, from the first location to the second location along the mesh, each cell distally adjacent to another cell has a strut with a smaller cross-sectional dimension than has a strut of the another cell.

58. The medical device of Clause 57, wherein each strut distally adjacent to another strut has a smaller cross-sectional dimension than has the another strut.

59. The medical device of Clause 57, wherein the cross-sectional dimension is a strut width.

60. The medical device of Clause 57, wherein the cross-sectional dimension is a strut thickness.

61. The medical device of Clause 57, wherein circumferentially adjacent struts have substantially the same cross-sectional dimension.

62. The medical device of Clause 56, wherein the first and second locations are longitudinally separated by a distance that is at least two thirds of the mesh length.

63. The medical device of Clause 56, wherein the first and second locations are longitudinally separated by a distance that is at least three quarters of the mesh length.

64. The medical device of Clause 56, wherein the first and second locations are longitudinally separated by a distance that is at least 90% of the mesh length.

65. A method for restoring localized blood flow in a cerebral blood vessel obstructed by a thrombus, comprising:
   delivering an intervention member through a microcatheter to a site of the thrombus in the cerebral blood vessel, the intervention member comprising a mesh configured to self-expand to assume an expanded configuration at the site, and to be changed to a compressed configuration for delivery through the microcatheter, the mesh configured to expand into the thrombus when transitioning from the compressed configuration to the expanded configuration;
   expanding the mesh at the site, by proximally withdrawing the microcatheter from over the structure, such that at least a portion of the mesh expands into the thrombus; and
   applying a proximally directed force to a proximal end of the mesh to collapse, prior to withdrawal of the intervention member into a catheter, a cell of a distal end of the mesh to at least the same extent as a cell of a portion of the mesh proximal of the distal end;
   removing at least a portion of the thrombus by retracting the intervention member.

66. The method of Clause 65, further comprising retracting the portion of the thrombus into a balloon catheter with the intervention member.

67. The method of Clause 65, wherein the intervention member is cylindrical in the absence of external forces.

68. The method of Clause 65, wherein the proximally directed force is applied to a proximal end of the mesh to collapse, prior to withdrawal of the intervention member into a catheter, a distal end of the mesh to a greater extent than the portion of the mesh proximal of the distal end.

69. The method of Clause 65, wherein collapsing the cell of the distal end of the mesh comprises reducing a maximum width of the cell of the distal end to at least the same extent as a maximum width of the cell of the portion of the mesh proximal of the distal end.

70. The method of Clause 65, further comprising gripping the thrombus with the cell of the distal end to at least the same extent as with the cell of the portion of the mesh proximal of the distal end.

71. The method of any of Clauses 65-70, performed with the device of any of Claims 1-64 or 69-75.

69. A medical device configured to perform an endovascular therapy, the device comprising:
    an elongate manipulation member comprising a distal end portion; and
    an intervention member comprising a proximal end portion and a mesh, the proximal end portion being coupled with the distal end portion of the elongate manipulation member, the mesh having a proximal mesh end, a distal mesh end, and a mesh length from the proximal end to the distal end, the mesh having a plurality of cells and being compressible to a collapsed configuration for delivery to an endovascular treatment site through a catheter and being self-expandable from the collapsed configuration to an expanded configuration, and wherein at least a portion of the mesh, from a first location to a second location along the mesh, is configured such that an amount of thrombus engagement in response to longitudinally directed tensile forces decreases by less than 5% or increases in a distal direction along the portion of the mesh, the first and second locations being longitudinally separated by a distance that is more than half of the mesh length.

70. The medical device of Clause 69, wherein the portion of the mesh, from the first location to the second location along the mesh, is configured such that the amount of thrombus engagement in response to longitudinally directed tensile forces does not decrease in a distal direction along the portion of the mesh.

71. The medical device of Clause 69, wherein the portion of the mesh, from the first location to the second location along the mesh, is configured such that the amount of thrombus engagement in response to longitudinally directed tensile forces increases in a distal direction along the portion of the mesh.

72. The medical device of Clause 69, wherein the first and second locations are longitudinally separated by a distance that is at least two thirds of the mesh length.

73. The medical device of Clause 69, wherein the first and second locations are longitudinally separated by a distance that is at least three quarters of the mesh length.

74. The medical device of Clause 69, wherein the first and second locations are longitudinally separated by a distance that is at least 90% of the mesh length.

75. The medical device of Clause 69, wherein the mesh is cylindrical in the absence of external forces.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 6A and 6B illustrate change in lateral cell width for various locations along expandable members.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. In some instances, well-known structures and components are shown in block diagram form in order to avoid obscuring the concepts of the subject technology.

Figure 1:
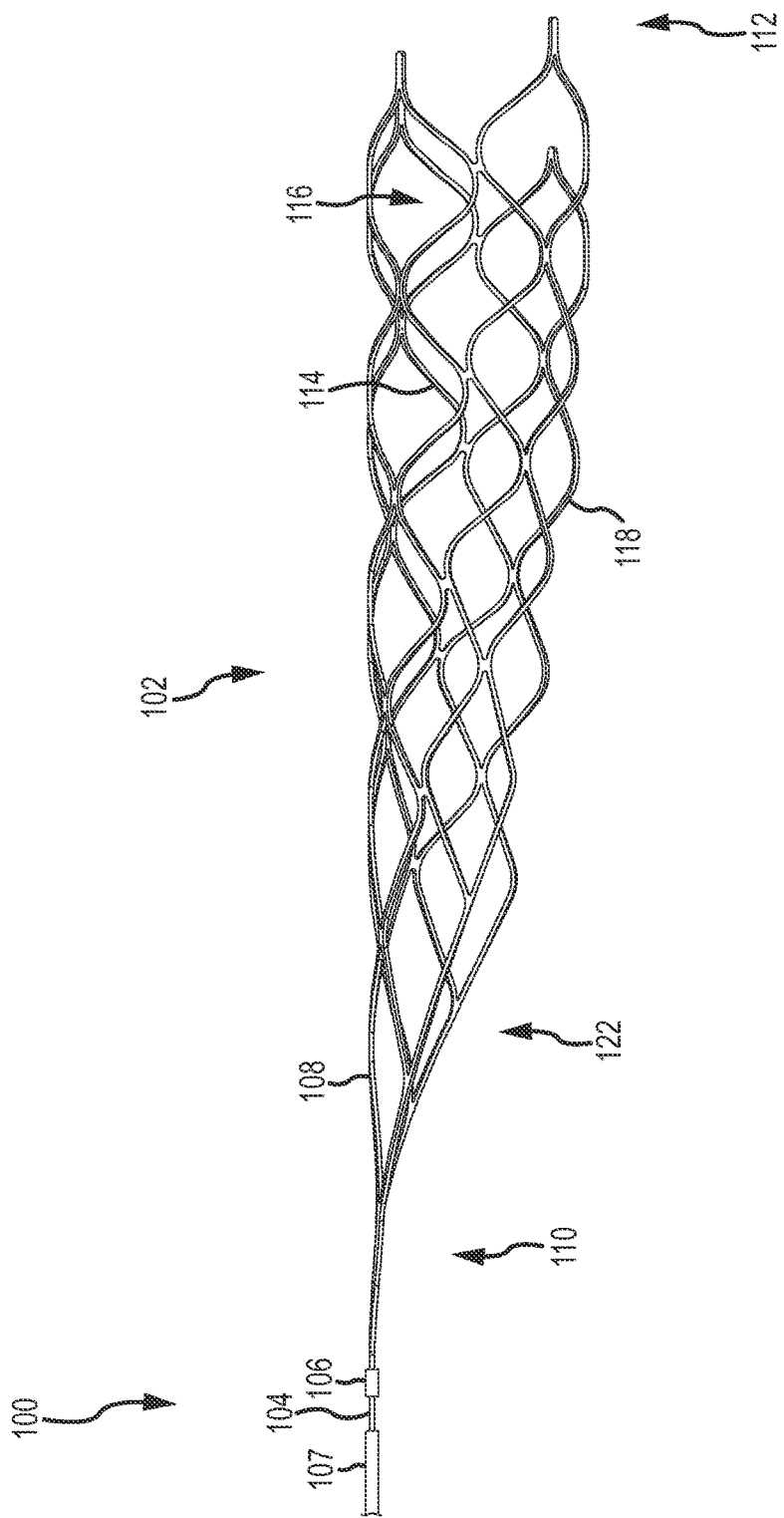
FIG. 1 illustrates a device, including an expandable member, for blood flow restoration, thrombus removal, or both, according to an embodiment.

FIG. 1 depicts a medical device 100 according to some embodiments of the subject technology. As illustrated in FIG. 1, the medical device 100 can comprise an expandable member 102 and a manipulation member 104. A proximal end portion of the expandable member 102 and a distal end portion of the manipulation member 104 can be joined at a connection 106. The manipulation member 104 can extend through a catheter 107 such that an operator can manipulate the expandable member 102, positioned within and/or distal to a distal end of the catheter 107, using the manipulation member 104 at a location proximal to a proximal end of the catheter 107.

The manipulation member 104 can have a length sufficient to extend from a location outside the patient's body through the vasculature to a treatment site within the patient's body. The manipulation member 104 can be monolithic or formed of multiple joined components. In some embodiments, the manipulation member 104 can comprise a combination of wire(s), coil(s), and/or tube(s). The manipulation member 104 can comprise one or more markers, e.g., comprised of radiopaque material(s) to aid radiographic visualization during manipulation.

The expandable member 102 and the manipulation member 104 can be substantially permanently attached together at the connection 106. That is, the expandable member 102 and the manipulation member 104 can be attached together in a manner that, under the expected use conditions of the assembly 100, the endovascular device and the manipulation member would not become unintentionally separated from one another.

Depending on the procedure and intended use of the medical device 100, it optionally may be advantageous to have a connection mechanism that permits intentional release of the medical device 100. For example, during a blood flow restoration procedure, it may prove difficult and/or dangerous to fully retrieve a thrombus due to a complicated vasculature or the risk of damaging a lumen wall. Leaving the medical device 100 inside the patient may prove to be the only option available to a surgeon or other medical personnel, or it may be a goal of the procedure, such as when the device 100 is deployed across an aneurysm (e.g., as an aneurysm bridge to retain coils or other materials in an aneurysm). In other circumstances the medical device 100 may include drug-eluting capabilities, and/or may be coated with a particular type of drug that facilitates thrombus dissolution. It may be advantageous in such circumstances to release the medical device 100 and allow the medical device 100 to anchor the thrombus against the lumen wall while the thrombus is dissolved by the drug. In some embodiments, the medical device 100 can comprise a portion, located proximally or distally of the connection 106, that is configured for selective detachment of the endovascular device 102 from the manipulation member 104. For example, such a portion can comprise an electrolytically severable segment of the manipulation member. In some embodiments, the assembly 100 can be devoid of any feature that would permit selective detachment of the endovascular device 102 from the manipulation member 104.

Further details regarding connections that can be employed between the expandable member 102 and the manipulation member 104 disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. patent application Ser. No. 13/834,945, entitled Connection of an Endovascular Intervention Device to a Manipulation Member, filed on Mar. 15, 2013, published as U.S. Patent Application Publication No. 2014/0194919 on Jul. 10, 2014; and U.S. patent application Ser. No. 13/835,130, entitled Connection of a Manipulation Member, Including a Bend without Substantial Surface Cracks, to an Endovascular Intervention Device, filed on Mar. 15, 2013, published as U.S. Patent Application Publication No. 2014/0194911 on Jul. 10, 2014; the entirety of each of which is hereby incorporated by reference herein.

Figure 2:
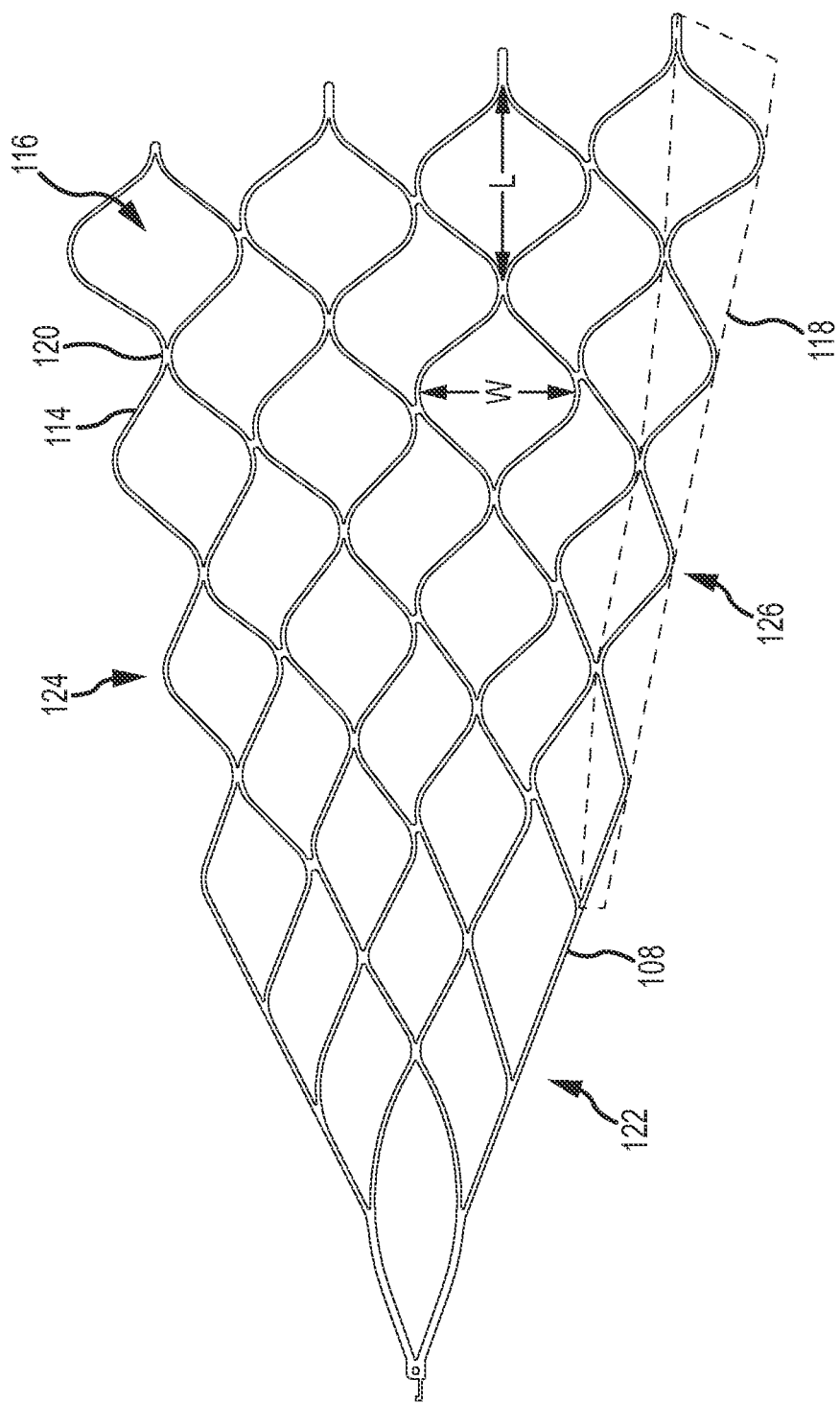
FIG. 2 illustrates an expandable member, according to an embodiment, in an unrolled state.
Figure 3:
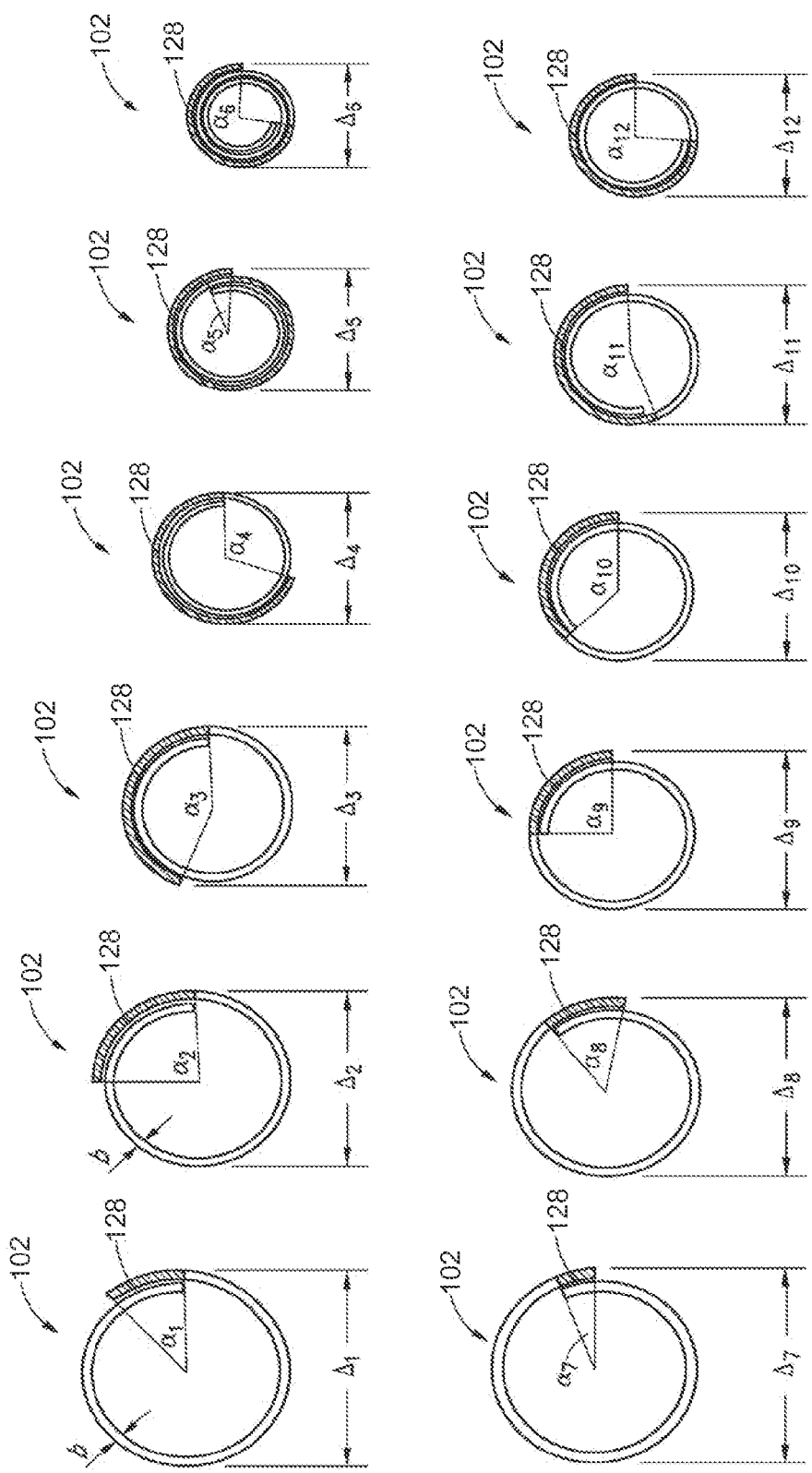
FIG. 3 is a schematic illustration of overlap configurations of the expandable member of FIG. 2, as viewed from a distal end of the expandable member.
Figure 4A:
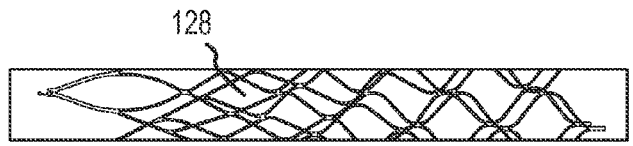
FIGS. 4A-D are schematic illustrations of overlap configurations of the expandable member of FIG. 2, as viewed from a side of the expandable member.
Figure 4B:
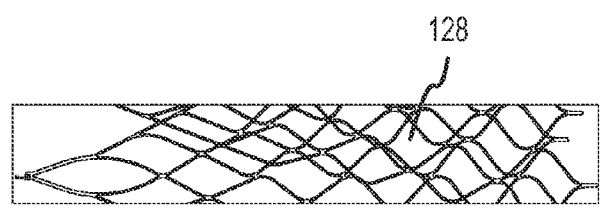
Figure 4C:
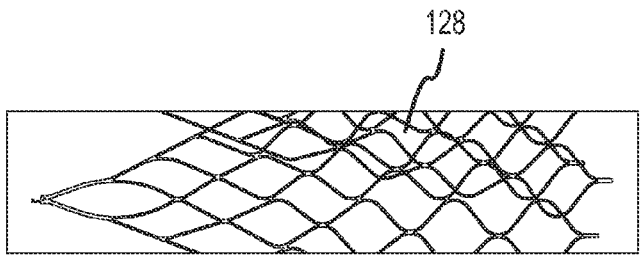
Figure 4D:
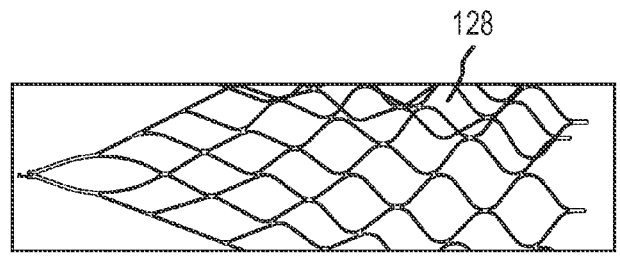

FIG. 2 is a plan view showing the expandable member 102 in an unrolled state to facilitate description and understanding. As illustrated in FIGS. 1 and 3, the expandable member 102 can have a tubular or generally cylindrical shape in absence of external forces in some embodiments. The expandable member 102 can be self-expanding, e.g. by super-elasticity or shape memory, or expandable in response to forces applied on the expandable member, e.g. by a balloon.

As illustrated in FIGS. 1 and 2, the expandable member 102 can comprise a frame 108 having a proximal end 110 and a distal end 112. The frame can comprise a plurality of struts 114 and a plurality of cells 116 forming a mesh. Groups of longitudinally and serially interconnected struts 114 can form undulating members 118 that extend in a generally longitudinal direction. The struts 114 can be connected to each other by joints 120. While the struts are shown having a particular undulating or sinuous configurations, in some embodiments the struts can have other configurations. The frame can have a generally tubular or generally cylindrical shape with one or both of the proximal end 110 and the distal end 112 being open.

As illustrated in FIGS. 1 and 2, a proximal portion 122 of the expandable member 102 can be tapered toward the proximal end 110. In some embodiments, the taper of the proximal portion can advantageously facilitate retraction and repositioning of the device 10 and expandable member 102. In some embodiments, the tapered proximal portion can also be designed to generally not contact the vessel wall during a blood flow restoration procedure, and to generally not interfere with the flow of blood within a vessel.

Individual cells of the proximal portion 122 can have different sizes than individual cells located distal to the tapered proximal portion. For example, in some embodiments, the proximal portion 122 can have individual cells that have a size larger than that of the individual cells located distal to the tapered proximal portion. The proximal portion 122 can taper gradually towards the connection 106.

The taper of proximal portion 122 can be at various angles relative to the manipulation member 104. For example, in some embodiments, the taper can have an angle of approximately 45 degrees relative to the manipulation member, though other angles are also possible.

The expandable member 102 can comprise a first edge 124 and a second edge 126. The first edge 124 and second edge 126 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 124, 126 can be curved, straight, or a combination thereof along the tapered proximal portion 122.

Referring to FIGS. 3 and 4A-D, the expandable member 102 can be curled, rolled, or otherwise formed such that first edge 124 and second edge 126 overlap one another when the expandable member 102 is in a volume-reduced form. In a volume-reduced form, the frame 102 of the expandable member 102 can overlap to facilitate introduction of the expandable member 102 into and through the catheter 107. In some embodiments, the expandable member 102 is circumferentially continuous (e.g., forming a continuous cylindrical shape), lacking first and second edges 124, 126 and having no overlap or gap in a volume-reduced form and expanded form. Regardless of whether the expandable member is circumferentially continuous, the expandable member 102 can have a central longitudinal axis both while in a volume-reduce form and when fully or partially expanded. In some embodiments, the expandable member 102 can be self-expandable, and can expand toward a fully expanded configuration upon release from the catheter 107. Upon expansion, the expandable member 102 can expand towards an inner wall of a vessel, towards a thrombus occluding the inner wall of a vessel, or both.

FIGS. 4A-4D illustrate various amounts of overlap of the frame 108 of the expandable member 102. The extent of any overlap of the frame 108 can depend upon a degree of the frame's expansion. Expansion within a vessel can be limited, at least in part, by the vessel's size, and the amount and the properties of any thrombus present. For example, a greater overlap of the edges 124, 126 can occur in narrower vessels, whereas in wider vessels the overlap can be smaller, or even an "underlap" may occur, in which case the edges 22 and 24 are separated by an open gap or space within the vessel.

With continued reference to FIGS. 3 and 4A-D, embodiments of the expandable member 102 can experience various degrees of overlap in a volume-reduced form, forming zones of overlap 128. The expandable member 102 can assume various diameters $\Delta_1$, $\Delta_2$, etc., depending on the degree of the overlap (e.g. represented by angle $\alpha_1$, $\alpha_2$, etc.). As illustrated in FIGS. 4A-D, the overlap zones 128 can vary in size and configuration depending on the vessel size. When inside a vessel, the overlap zone of the expandable member 102 can advantageously provide grip and/or retaining ability with respect to a thrombus. For example, when the expandable member 102 expands against a thrombus, the individual struts 114 and individual cells 116 of the overlap zone can embed into and grip, or retain, the thrombus. Alternatively, the expandable member 102 can be constructed without any overlap or edges 124, 126, e.g. as a continuous tubelike or cylindrical member.

The expandable member 102 can be manufactured in various lengths and relaxed-state diameters. In some embodiments, the expandable member 102 can have lengths, measured proximally to distally along the longitudinal axis, of 15 mm or less to 40 mm or more, though other ranges and sizes are also possible. The expandable member 102 can also have relaxed-state diameters, the diameters being measured when the expandable member 102 is fully free to expand, i.e., in absence of external forces. In some embodiments, the expandable member 102 can have a diameter of approximately 3 mm to 4 mm so as to be used in size 18 microcatheters (i.e. microcatheters with an inner diameter of approximately 0.21 inch). In some embodiments the expandable member 102 can have a diameter of approximately 5 mm to 6 mm so as to be used in size 27 microcatheters (i.e. microcatheters with an inner diameter of approximately 0.027 inch). Other ranges and values are also possible.

Each cell 116 of the expandable member 102 can have a maximum length (labeled "L" in FIG. 2), as measured along a longitudinal axis of the expandable member 102, and a maximum width W, as measured along a direction generally perpendicular to the length (labeled "W" in FIG. 2). In some embodiments, cell size and dimensions can vary, as can the individual filament thicknesses and widths.

The location and longitudinal extent of thrombus engagement by a mechanical thrombus-retrieval device, e.g., the expandable member 102, can affect the likelihood of successfully capturing the engaged thrombus. Some embodiments of the subject technology increase the likelihood of successful thrombus capture and retrieval by increasing a longitudinal extent of substantially even thrombus engagement, distally shifting the region of increased thrombus engagement, or both. When a thrombus is primarily engaged along a portion of the thrombus near its proximal end, and particularly when a longitudinal extent of substantially even thrombus engagement is small, the thrombus may be more likely to fragment, become released from the retrieval device, or both.

In some embodiments, the expandable member 102 can be configured for substantially uniform or distally biased thrombus engagement, after expansion of the expandable member 10 into the thrombus, during retrieval of thrombus from a vessel by proximal retraction of the manipulation member 104. The thrombus can be generally soft, or malleable, or generally hard, or callous. For example, the expandable member 102 can have strut and cell dimensions that provide substantially uniform or distally biased thrombus engagement.

Figure 5:
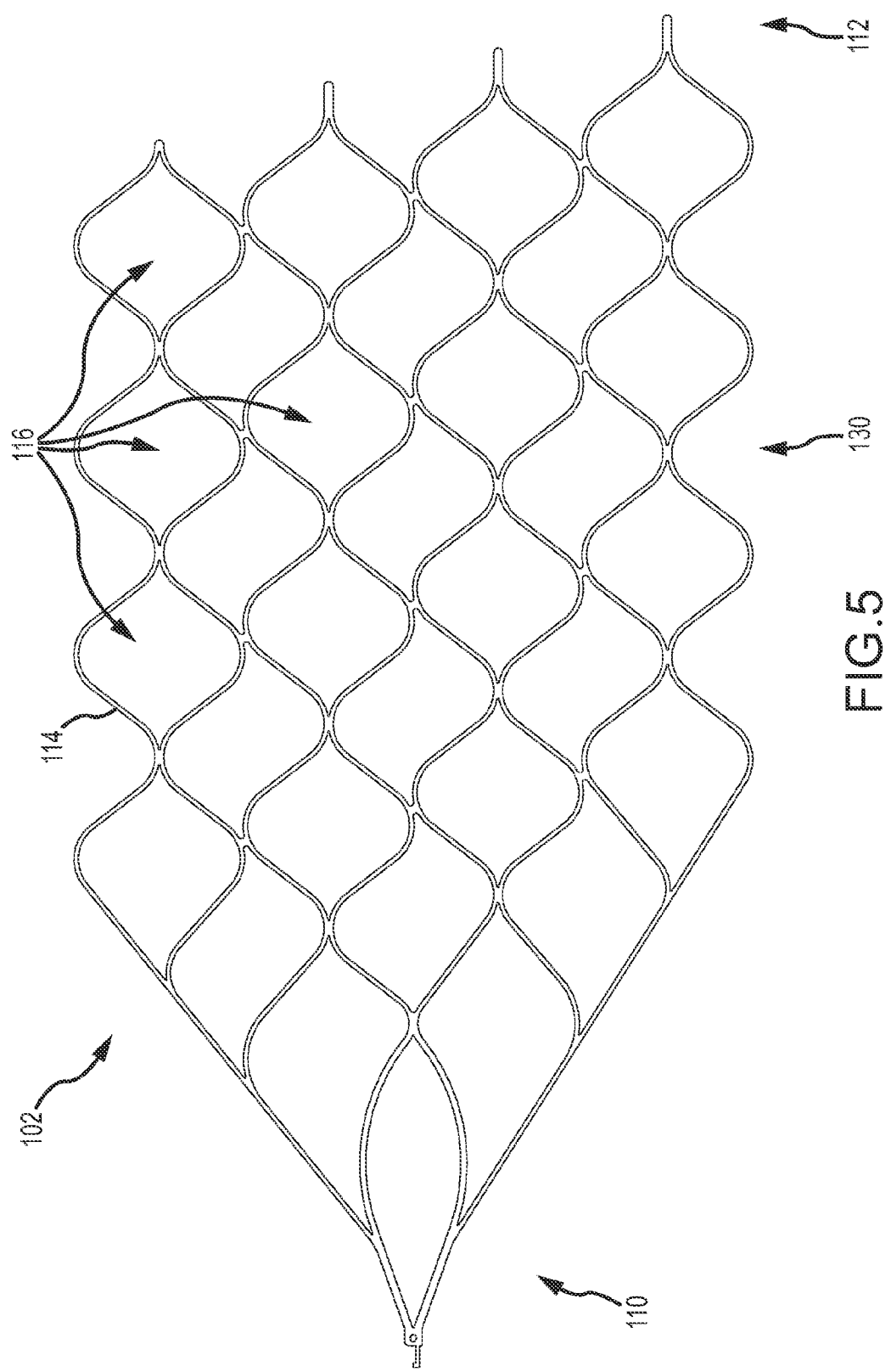
FIG. 5 illustrates an expandable member in an unrolled state.

FIG. 5 illustrates an expandable member 102 having a pattern 130 of cells 116 of substantially uniform dimensions and of struts 114 of substantially uniform dimensions. The pattern of cells and struts of FIG. 5 is substantially uniformly flexible or deformable. However, when the expandable member of FIG. 5 is embedded in a thrombus and a proximally directed force is applied at a proximal end 110 of the expandable member, the cells of the expandable member tend to collapse in width, and therefore engage a thrombus, more along a proximal portion of the substantially uniform pattern 130 than they do along a distal portion of the substantially uniform pattern 130. Such a proximally directed force may be considered to simulate the force exerted on the proximal end 110, via the manipulation member 104, during retrieval of the expandable member 102 in a procedure to remove, e.g., thrombus from a blood vessel.

FIGS. 6A and 6B illustrate the amount of change (reduction) in (e.g., maximum) cell width W observed for cells in various longitudinal positions along the length of the frame 108, upon application of a proximally directed force at a proximal end of the frame when embedded in simulated thrombus having an outer extent fixed in six degrees of freedom. FIG. 6A is an exemplifying plot of the amount of change (reduction) in (maximum) cell width (resulting from such force application) against longitudinal position for a frame having a substantially uniform cell angle or pattern 130. As indicated by FIG. 6A, the amount of change in maximum cell width diminishes with distance from the proximal end for a frame having a substantially uniform pattern 130. Thus, an expandable member having a substantially uniform pattern 130 "pinches" the thrombus more (by virtue of a greater reduction in cell width) along a proximal portion of the thrombus than it does along a distal portion of the thrombus.

FIG. 6B is an exemplifying plot of the amount of change (reduction) in (maximum) cell width against the longitudinal position for frames in some embodiments of the subject technology, for example such as those illustrated in FIGS. 2, 8, 9, and 10. In contrast to FIG. 6A, FIG. 6B indicates that the amount of reduction in maximum cell width increases with distance from the proximal end for frames according to some embodiments of the subject technology. Thus, an expandable member according to some embodiments of the subject technology pinches and grips the thrombus more along a distal portion of the thrombus than it does along a proximal portion of the thrombus. Therefore, expandable members according to some embodiments of the subject technology can be less likely to fragment the thrombus, release the thrombus, or both during retrieval, compared to an expandable member having a substantially uniform pattern 130.

Figure 7A:
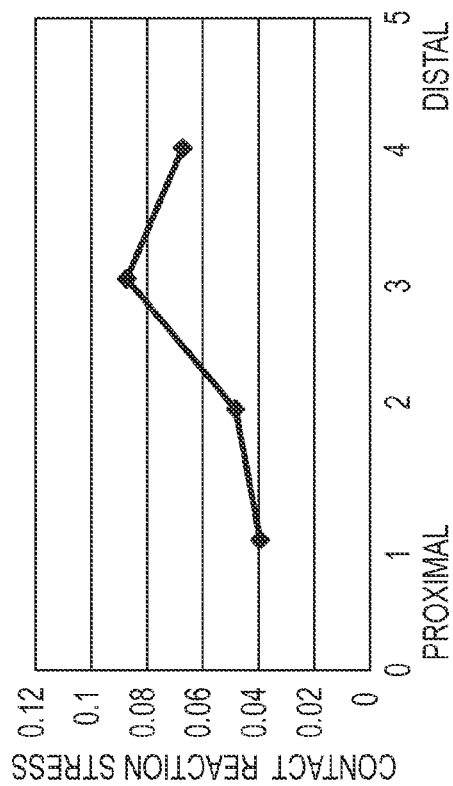
FIGS. 7A and 7B illustrate associated contact reaction stress of the clot for various locations along expandable members, as a consequence of the change in lateral cell width illustrated in FIGS. 6A-6B.
Figure 7B:
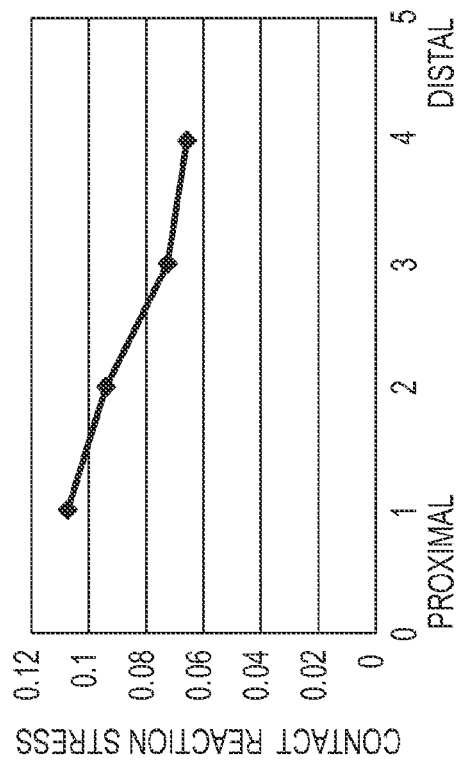

FIGS. 7A and 7B indicate the resultant contact reaction stresses (due to the cell width reduction) between the frame and thrombus in cells at various longitudinal positions along the length of the frame, upon application of a proximally directed force at a proximal end of the frame when embedded in simulated thrombus having an outer extent fixed in six degrees of freedom. FIG. 7A is an exemplifying plot of contact reaction stress against longitudinal position for a frame, as illustrated in FIG. 5 for example, wherein longitudinally and laterally adjacent cells have substantially the same dimensions and the struts surrounding those cells have substantially the same dimensions. As indicated by FIG. 7A, contact reaction stress diminishes with distance from the proximal end for a frame having a substantially uniform pattern 130. Thus, an expandable member having a substantially uniform pattern 130 tends to pull on the thrombus, during retraction, more along a proximal portion of the thrombus than it does along a distal portion of the thrombus.

FIG. 7B is an exemplifying plot of contact reaction stress against longitudinal position for frames in some embodiments of the subject technology, for example such as those illustrated in FIGS. 2, 8, 9, and 10. In contrast to FIG. 7A, FIG. 7B indicates that contact reaction stress increases, along at least a portion of the frame's length, with distance from the proximal end for frames according to some embodiments of the subject technology. Thus, an expandable member according to some embodiments of the subject technology tends to pull on the thrombus less along a proximal portion of the thrombus than it does along a portion of the thrombus distal to the proximal portion. Therefore, expandable members according to some embodiments of the subject technology can be less likely to fragment the thrombus, release the thrombus, or both during retraction, compared to an expandable member having a substantially uniform pattern 130.

Figure 8:
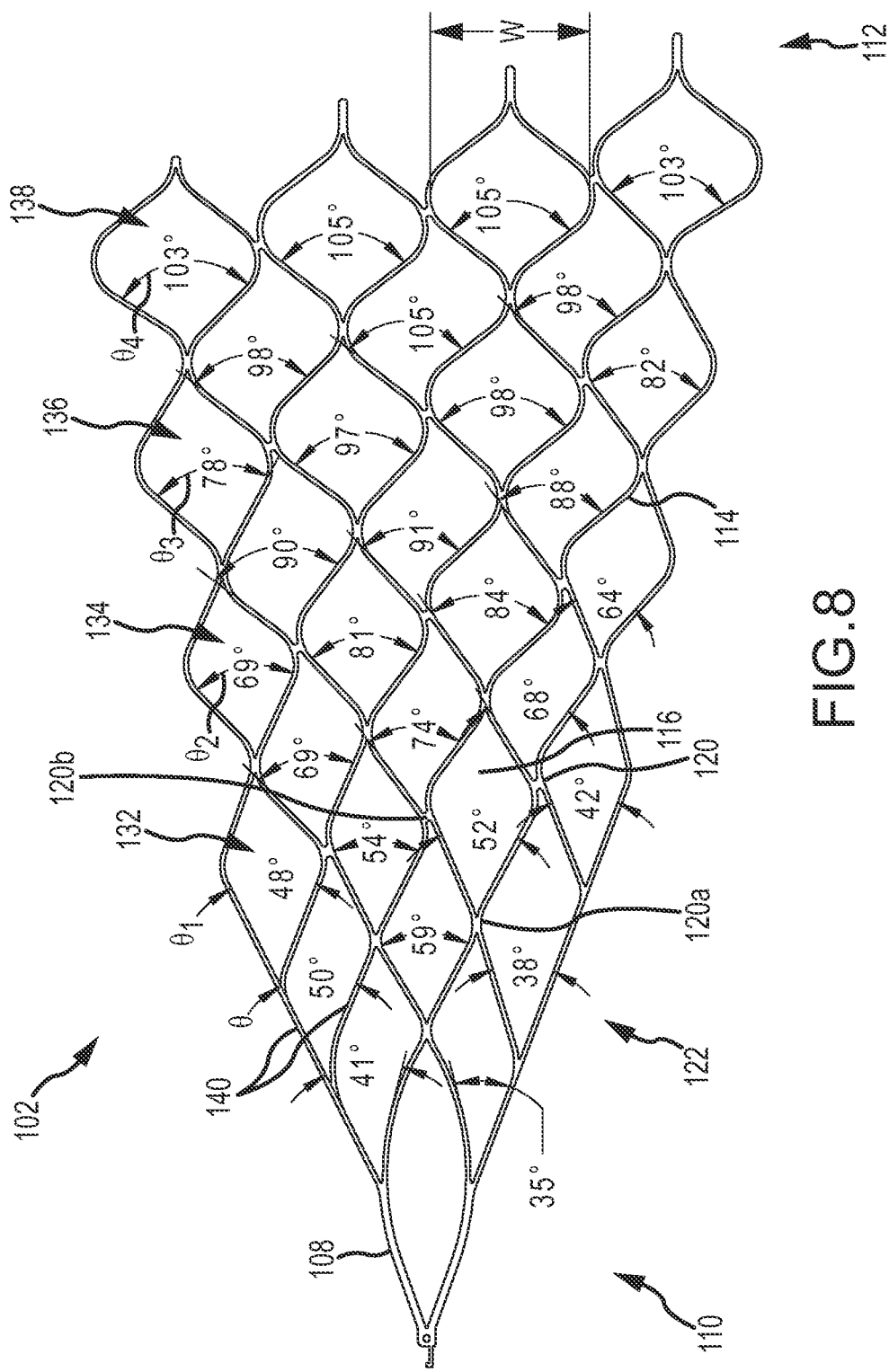
FIG. 8 illustrates an expandable member, according to an embodiment, in an unrolled state.
Figure 9:
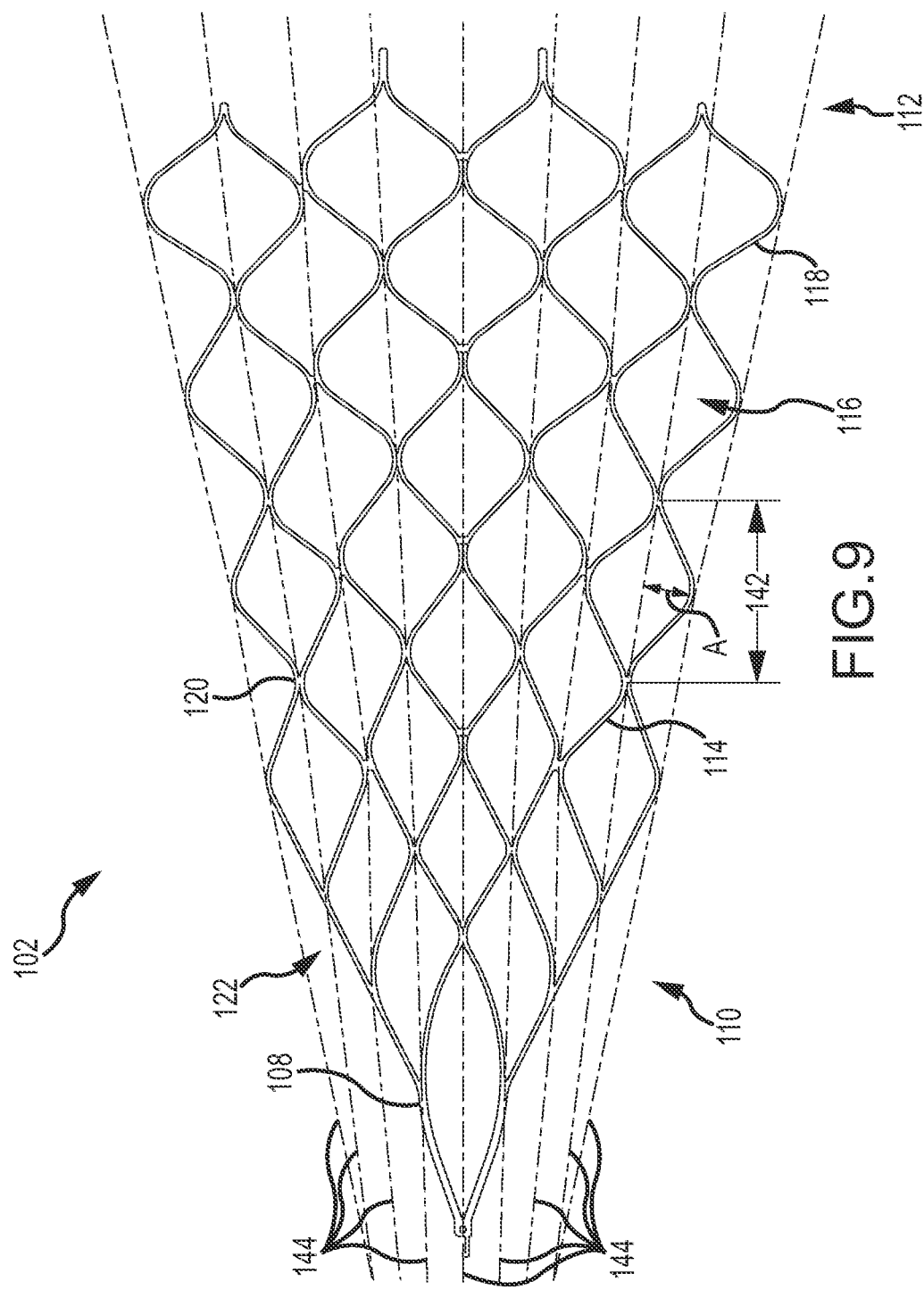
FIG. 9 illustrates an expandable member, according to an embodiment, in an unrolled state.
Figure 10:
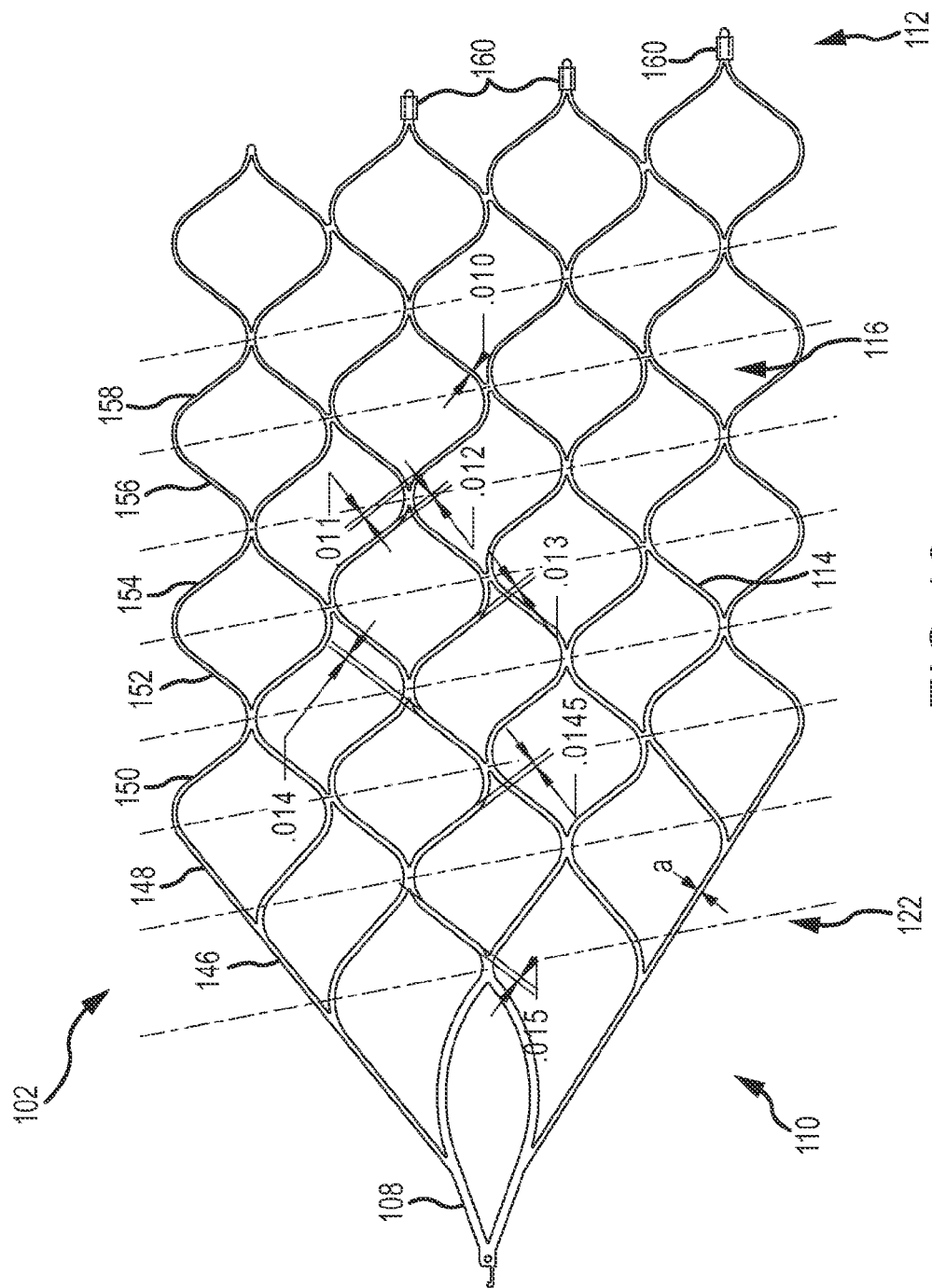
FIG. 10 illustrates an expandable member, according to an embodiment, in an unrolled state.

FIGS. 8-10 illustrate expandable members 102, according to embodiments of the subject technology, in plan view, e.g., an unrolled state. The expandable members 102 of FIGS. 8-10 are examples of the expandable member 102 described above with reference to FIGS. 2-4D. Accordingly, the description of the expandable member 102 with reference to FIGS. 2-4D also applies to expandable members 102 of FIGS. 8-10.

The expandable members 102 of FIGS. 8-10 can provide distally biased thrombus engagement, as described above with reference to FIGS. 6B and/or 7B, substantially uniform thrombus engagement, or a combination thereof over lengthwise portions of the expandable member. Thrombus engagement can be considered substantially uniform when the amount of change in maximum cell width and/or contact reaction stress varies in the longitudinal direction by less than 5% upon application of a proximally directed force at a proximal end of the expandable member when the expandable member is embedded in thrombus, or simulated thrombus, having an outer extent fixed in six degrees of freedom.

In some embodiments, at least a portion of the frame 108, from a first location to a second location along the frame, is configured such that an amount of cell deformation or deflection in response to longitudinally directed tensile forces decreases by less than 5% or increases in a distal direction along a portion of the frame. The cell deformation can be, for example, change of maximum cell width. In some embodiments, the amount of cell deformation in response to longitudinally directed tensile forces does not decrease in a distal direction along the portion of the frame. In some embodiments, the amount of cell deformation in response to longitudinally directed tensile forces continuously increases in a distal direction along the portion of the frame. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, at least a portion of the frame 108, from a first location to a second location along the frame, is configured such that an amount of thrombus engagement in response to longitudinally directed tensile forces decreases by less than 5% or increases in a distal direction along a portion of the frame. The thrombus engagement can be, for example, contact reaction stress. In some embodiments, the amount of thrombus engagement in response to longitudinally directed tensile forces does not decrease in a distal direction along the portion of the frame. In some embodiments, the amount of thrombus engagement in response to longitudinally directed tensile forces continuously increases in a distal direction along the portion of the frame. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

FIG. 8 illustrates an expandable member 102 wherein, in a portion of the frame 108 in a relaxed state, each cell distally adjacent to another cell, in a longitudinal row of cells, has a larger proximal inscribed strut angle $\theta$ between first and second struts (i) bounding a proximal portion of the cell and (ii) diverging in a distal direction, than has the another cell. For example, FIG. 8 shows a first cell 132 having a proximal inscribed strut angle $\theta_1$, a second cell 134 having a proximal inscribed strut angle $\theta_2$, a third cell 136 having a proximal inscribed strut angle $\theta_3$, and a fourth cell having a proximal inscribed strut angle $\theta_4$, wherein $\theta_4 > \theta_3 > \theta_2 > \theta_1$. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, the proximal inscribed strut angle $\theta$ can be measured between substantially straight portions 140 of the struts 114, as illustrated in FIG. 8. In some embodiments, the proximal inscribed strut angle $\theta$ can be measured between straight reference lines that connect a joint 120a, at a proximal end of a cell, with opposing laterally positioned joints 120b, 120c, respectively, at of that cell. In either case, each strut 114 can be straight, curved, or comprise straight portion(s) and curved portion(s).

In addition or alternative to distally increasing, proximal inscribed strut angles, the expandable member 102 can have a portion of the frame 108 wherein, in a relaxed state, each cell distally adjacent to another cell, in a longitudinal row of cells, has a larger interior bounded area than has the another cell. For example, an interior bounded area of fourth cell 138 can be larger than an interior bounded area of third cell 136, which can be larger than an interior bounded area of second cell 134, which can be larger than an interior bounded area of first cell 132. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, the expandable member 102 can have a portion of the frame 108 wherein, in a relaxed state, each cell distally adjacent to another cell, in a longitudinal row of cells, has a larger maximum cell width W than has the another cell. For example, a maximum cell width of fourth cell 138 can be larger than a maximum cell width of third cell 136, which can be larger than a maximum cell width of second cell 134, which can be larger than a maximum cell width of first cell 132. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

Accordingly, the herein-discussed configurations of the expandable member 102 (distally increasing maximum cell width W, distally increasing cell area, distally increasing proximal included strut angle θ, distally increasing amplitude A, distally diverging reference lines 144, and/or distally increasing strut flexibility/deflectability) can each be considered a means for engaging a thrombus (or other material) in a substantially uniform (and/or distally biased) manner along the length of the expandable member 102.

In the embodiment of FIG. 8, maximum cell length can range from 3.50 mm to 5.50 mm in a relaxed state, though other ranges and values are also possible, and maximum cell width can range from between 2.50 mm to 4.50 mm and a relaxed state, though other ranges and values are also possible. All of the foregoing dimensions can optionally be implemented alone or in any combination without departing from the scope of this disclosure.

FIG. 9 illustrates an expandable member 102 comprising a plurality of undulating or sinuous members 118. Each undulating or sinuous member 118 can comprise a plurality of oscillations 142. Each oscillation can have an amplitude (labeled "A" in FIG. 9). In some embodiments, an oscillation can correspond in length to the length of a cell. An oscillation 142 can comprise one or more struts 114. Some embodiments can comprise a portion of the frame 108 wherein, in a relaxed state, each oscillation of each undulating or sinuous member 118 does not decrease, or alternatively, increases in a distal direction compared to a proximally adjacent oscillation. In some embodiments, the amplitude of the oscillations can increase distally at a constant rate per unit length. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

FIG. 9 illustrates a plurality of reference lines 144. Each reference line can pass through all joints 120 between adjacent cells in a row of cells. Some embodiments can comprise a portion of the frame 108 wherein, in a relaxed state, each reference line 144 continuously diverges from at least one or two adjacent reference lines 144. In some embodiments, the reference lines can be straight. In some embodiments, all or a portion of respective reference line can be curved. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, the portion of the frame can comprise a longitudinal row of at least two, three, or four cells.

In some embodiments, the expandable member 102 can have a portion of the frame 108 wherein, in a relaxed state, each cell distally adjacent to another cell can have a strut that is more flexible or deflectable than a strut of the another cell. In some embodiments, each strut distally adjacent to another strut can be more flexible or deflectable than is the another strut. Strut flexibility or delectability can be increased, for example, by diminishing strut thickness, strut width, or both along all or a portion of the strut's length. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

The struts 114 can have individual strut widths "a" (FIG. 10) that range from 0.010 in. to 0.025 in., and individual strut thicknesses "b" that range from 0.045 mm to 0.080 mm, though other ranges and values for individual strut width and thickness are also possible. Widths "a" as described herein can generally be measured as illustrated by the arrows in FIG. 10. Thicknesses "b" as described herein can generally be measured as illustrated by the arrows in FIG. 3 (e.g. in a direction extending out of the page of FIG. 10, and perpendicular to the measurement for width "a"). The widths "a" can be measured, for example, using a system such as the Visicon Automated Inspection System, or other suitable system. The thicknesses "b" can be measured, for example, using a system such as the Heidenhain Inspection System, or other suitable system.

With continued reference to FIG. 10, the joints 120 can have an individual strut thickness "b" that range from 0.050 mm to 0.0825 mm and an individual strut width "a" that ranges from 0.050 mm to 0.0825 mm, though other ranges and values are also possible. In some embodiments, individual struts can have individual strut thicknesses "b" that range from 0.040 mm to 0.075 mm, and individual strut widths "a" that range from 0.038 mm to 0.082 mm, though other ranges and values are also possible. In some embodiments, the individual struts in a portion of the expandable member 102 can have average strut thicknesses "b" that range from 0.048 mm to 0.067 mm, and individual strut widths "a" that average from 0.053 mm to 0.067 mm, though other ranges for average values are also possible.

FIG. 10 illustrates an example of an embodiment wherein strut thickness is diminished in a distal direction, thereby distally increasing strut flexibility or to flexibility. The frame 108 of the expandable member 102 in FIG. 10 comprises a plurality of rings 146, 148, 150, 152, 154, 156, 158 of circumferentially adjacent struts. The struts 114 in each ring can have substantially the same width, as illustrated, for example, in FIG. 10. In some embodiments, circumferentially adjacent struts can have different widths. Referring again to FIG. 10, the strut width of each ring 146, 148, 150, 152, 154, 156, 158 can diminish in the distal direction. In other words, a strut width of ring 158 can be less than a strut width of ring 156, which can be less than a strut width of ring of 154, which can be less than a strut width of ring 152, which can be less than a strut width of ring 150, which can be less than a strut width of ring 148, which can be less than a strut width of ring 146. In some embodiments, two or more longitudinally adjacent struts, or rings of struts, can have the same, or substantially the same, width. For example, struts 114 distal to the ring 158 can have the same, or substantially the same, strut width as the struts of ring 158.

Although FIG. 10 illustrates the struts 114 as having substantially constant widths along their entire respective lengths, the struts can have widths that vary along their lengths in some embodiments. For example, the struts can have an hourglass shape, can be wider in the middle than at the ends, can have corrugated edges, or have other configurations. Strut thickness can likewise be constant or variable along each strut's length. The struts' cross-sectional areas can likewise be constant or variable along each strut's length.

In the embodiment of FIG. 10, maximum cell length can range from 3.50 mm to 5.50 mm in a relaxed state, though other ranges and values are also possible and within the scope of this disclosure, and maximum cell width can range from between 2.50 mm to 4.50 mm and a relaxed state, though other ranges and values are also possible and within the scope of this disclosure.

The expandable member 102 can generate specific forces once it is deployed and released from the catheter 107 for engagement and removal of thrombi. By deploying the expandable member 102 in or across a thrombus, the expandable member 102 can be expanded, e.g., self-expanded to a larger diameter due to elastic energy stored in the expandable member 102. The expandable member 102 can expand in the vessel until equilibrium is reached between the stored elastic energy and an opposing force from the surrounding vessel wall and/or thrombus. The struts 114 and cells 116 of the expandable member 102 can penetrate a thrombus, promoting adhesion and embedment of the thrombus to the expandable member 102, and the expanding force of the expandable member 102 can promote dislodgment of the thrombus from the vessel wall.

For example, the stored elastic energy of the expandable member 102 can generate outward forces known as radial force (RF) and chronic outward force (COF). The radial force is equivalent to the outward force exerted by the expandable member 102 during compression of the expandable member 102. The chronic outward force is equivalent to the outward force exerted by the expandable member 102 during decompression, or expansion, of the expandable member 102. In a preferred arrangement, the COF can be designed so that it is not so high that it bursts, or damages, a vessel wall. In a preferred arrangement, the RF can be designed so that it is high enough to resist compression forces from the surrounding vessel environment, maintain patency of the vessel lumen, and restore flow through the thrombus site.

During deployment and thrombus retrieval, the highest COF and RF can occur when the expandable member 102 is deployed and/or retrieved inside a minimum recommended diameter vessel. Conversely, the COF and RF can be the lowest when the expandable member 102 is deployed and/or retrieved inside a maximum recommended diameter vessel. In some embodiments, a curled, overlapped expandable member 102 can enhance the COF and RF, particularly in smaller diameter vessels, to allow for increased embedment of a thrombus to the expandable member 102.

The radial force can be measured by various methods. For example, a two pin method can measure the radial force by placing (e.g. sliding) the expandable member 102 over two elongate, parallel pins, such that the generally tubular, expandable member 102 encompasses and surrounds the two pins. When placed over the two pins, the proximal end 110 of proximal portion 122 can be located generally halfway between the two elongate pins, and to one side. The ends of the two pins can be placed in a tensile testing machine. When the testing machine is loaded, the machine can cause the pins to pull apart from one another, such that a force is imparted on the expandable member 102. When the expandable member 102 slips off of one of the pins, the radial force can be measured.

A thin film method can also be used to measure the radial force, and can additionally be used to measure the chronic outward force. The thin film method can generally comprise compressing and decompressing the expandable member 102 circumferentially 360 degrees using a thin film of PTFE wrapped around the expandable member 102. The thin film method can measure changes in diameter of the expandable member 102 versus force for both expansion and contraction of the expandable member 102.

In a preferred arrangement using the thin film method, the expandable member 102 can have a radial force measurement greater than or equal to 0.0010 N per mm of length of the portion of the expandable member 102 that is configured to contact a vessel wall or thrombus (e.g. distal portion 30). The length in this unit refers to a proximal to distal direction measurement (i.e. moving left to right in FIG. 1). Instead of or in addition to the foregoing, the expandable member 102 can have a chronic outward force of less than or equal to 0.026 N per mm (or between about 0.001 N/mm and 0.026 N/mm) of length of the portion of the expandable member 102 that is configured to contact a vessel wall or thrombus, depending on the inner diameter of the vessel in which the expandable member is deployed. In a preferred arrangement using the two pin method, the expandable member 102 can have a radial force measurement of between approximately 6 to 37 (or between approximately 0 to 50) gf per inch of length of the portion of the expandable member 102 that is configured to contact a vessel wall or thrombus. Other values for the foregoing variables are possible and within the scope of this disclosure.

In some embodiments, the expandable member 102 can further include at least one distal marker 160. The distal marker 160 can be attached to or integrally formed with a distal portion of the expandable member 102. The distal marks 160 can comprise, for example, a band comprising platinum, gold, and/or other radiopaque materials. The markers 160 can be used during an imaging process to identify a location or locations of the expandable member 102 during a blood flow restoration procedure. PCT Publication No. WO 2009/105710, which is incorporated by reference in its entirety, describes various uses of marker bands and imaging of an expandable member 102.

The frame 108 can be formed, for example, by cutting a sheet or tube (e.g., by laser, etching, etc.), by interconnecting a multitude of filaments by laser welding, or by other suitable methods. In some embodiments, the expandable member 102 can be initially laser cut from a tube. In some embodiments, the expandable member 102 can be formed by cutting a pattern on a flat sheet and then rolling the flat sheet into a generally tube-like or coiled shape. The joints 120 may be formed by welding, soldering, or otherwise joining the struts 114. Other methods for forming the expandable member 102 are also possible.

In some embodiments, the expandable member 102 can comprise metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bio-analogous polymers, tungsten, tantalum, platinum, polymers, bio-polymers, ceramics, bio-ceramics, or metallic glasses. Part or all of the expandable member may elute over time substances such as drugs, biologics, gene therapies, antithrombotics, coagulants, anti-inflammatory drugs, immunomodulator drugs, anti-proliferatives, migration inhibitors, extracellular matrix modulators, healing promoters, re-endothelialization promoters, or other materials. In some embodiments, the expandable member may be formed from materials having shape memory properties. In some embodiments, the expandable member may be finished by processes to remove slag. In some embodiments, the expandable member may be subjected to a tempering treatment at temperatures customarily applied to the material so that the impressed structure is permanently established.

Figure 11A:
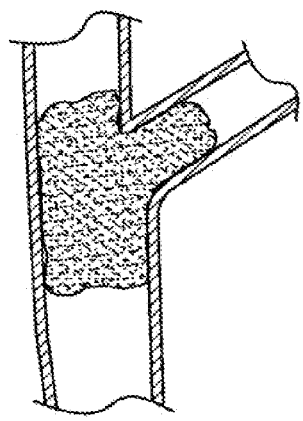
FIGS. 11A-11D schematically illustrate thrombi located in various vessel arrangements.
Figure 11B:
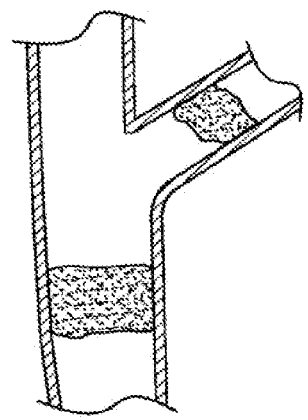
Figure 11C:
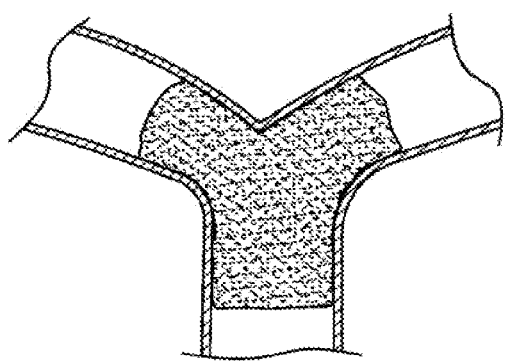
Figure 11D:
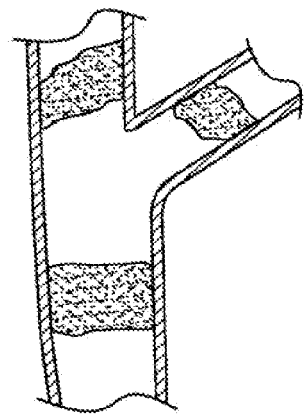

Referring to FIGS. 11A-D, in some embodiments the expandable member 102 can be used as a flow restoration device and/or an implantable member (e.g. stent) in a vessel, including at bifurcation, bi-vessel, and/or multi-vessel locations. For example, and with reference to FIG. 11A, thrombi can be located at bifurcations in the neurovasculature such as the internal carotid artery and the anterior cerebral artery, or internal carotid artery and middle cerebral artery, or the basilar artery and the posterior cerebral artery. With reference to FIG. 11B, thrombi can also be located at two vessels (i.e. bi-vessels) as two separate clots in similar vessels. With reference to FIGS. 11C and 11D, thrombi can also be located at multi-vessels as one clot that is within multiple vessels or as multiple clots that are within multiple vessels. Vessels with such clots can be located, for example, at the intracranial internal carotid, anterior cerebral and middle cerebral arteries, and basilar artery and both posterior and cerebral arteries.

Figure 12:
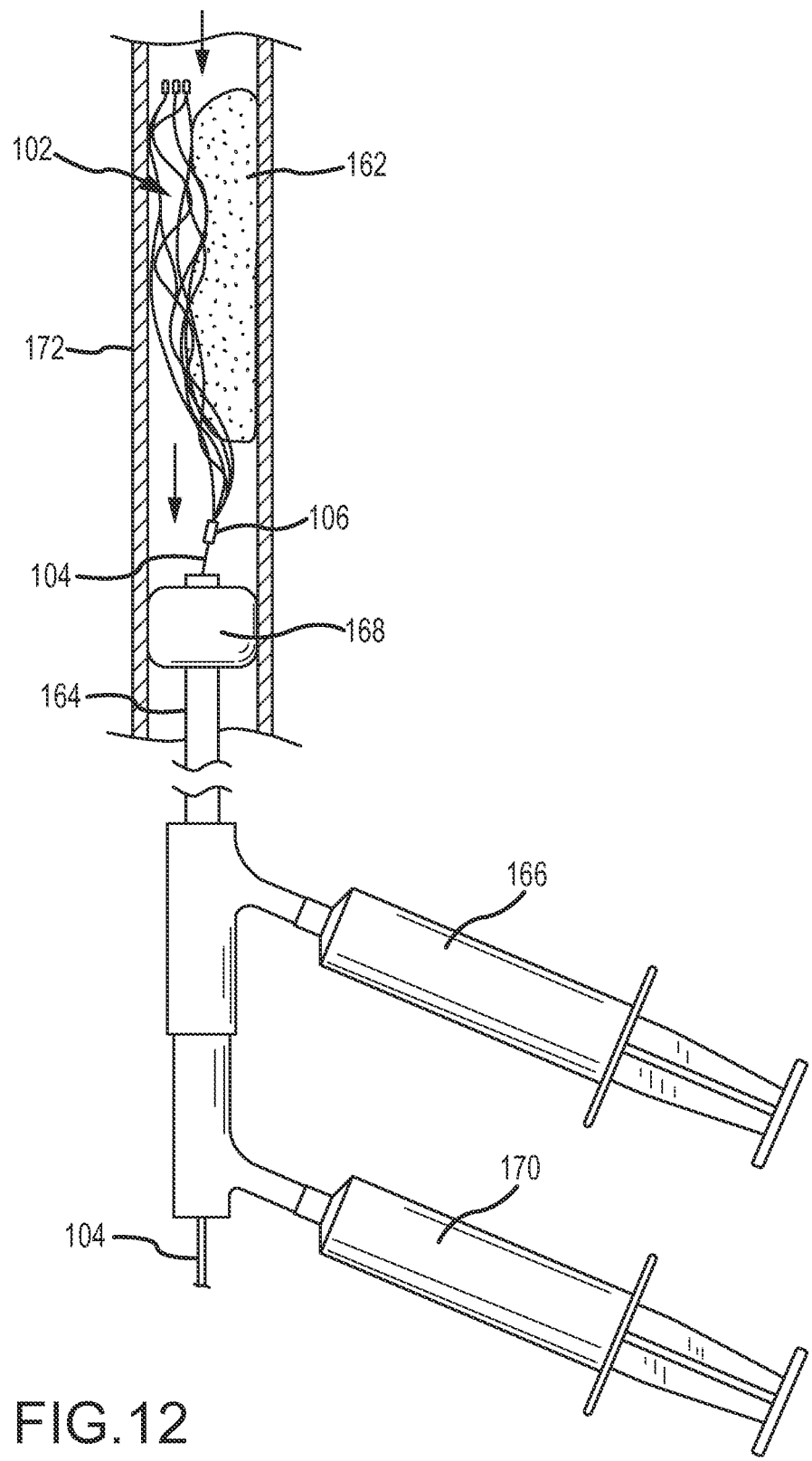
FIG. 12 schematically illustrates a system for blood flow restoration, thrombus removal, or both.

Referring to FIG. 12, the medical device 100 can be used in a system with a balloon guide catheter 164, with a syringe 166 for expanding a balloon 168, a syringe 170 for aspiration, or both. Aspiration assistance can enable flow reversal through the expandable member 102 and thrombus 162. Inflation of the balloon 168 can impede or prevent flow proximally through the vessel from the balloon 168 towards the expandable member 102. As part of the retrieval procedure, continuous aspiration can be employed through the balloon guide catheter 164, with vigorous aspiration when the expandable member 102 is near a distal tip of the balloon guide catheter. The aspiration with flow reversal can help allow the distal vasculature to continue to have blood perfusing through the vessels during the retrieval process, and can inhibit the possibility of distal emboli. There can be an advantage to having blood flow across the expandable member 102 and thrombus 162 with the potential of natural lysing of blood and increased surface area for thrombus dissolving medicines, if they are provided. The aspiration with flow reversal can also assist in the thrombus retrieval process by aiding in the removal of the thrombus 162. The flow can be directed towards a lumen of the balloon guide catheter 164 due to the aspiration. The expandable member 102 and thrombus 162 can thus be assisted by the flow to enter the lumen of the balloon guide catheter 164. In some embodiments, if withdrawal into the balloon guide catheter 164 is difficult for any reason during aspiration, the balloon 168 can be deflated, and the balloon guide catheter 164, catheter 107, and expandable member 102 can be withdrawn simultaneously while maintaining aspiration.

Figure 13:
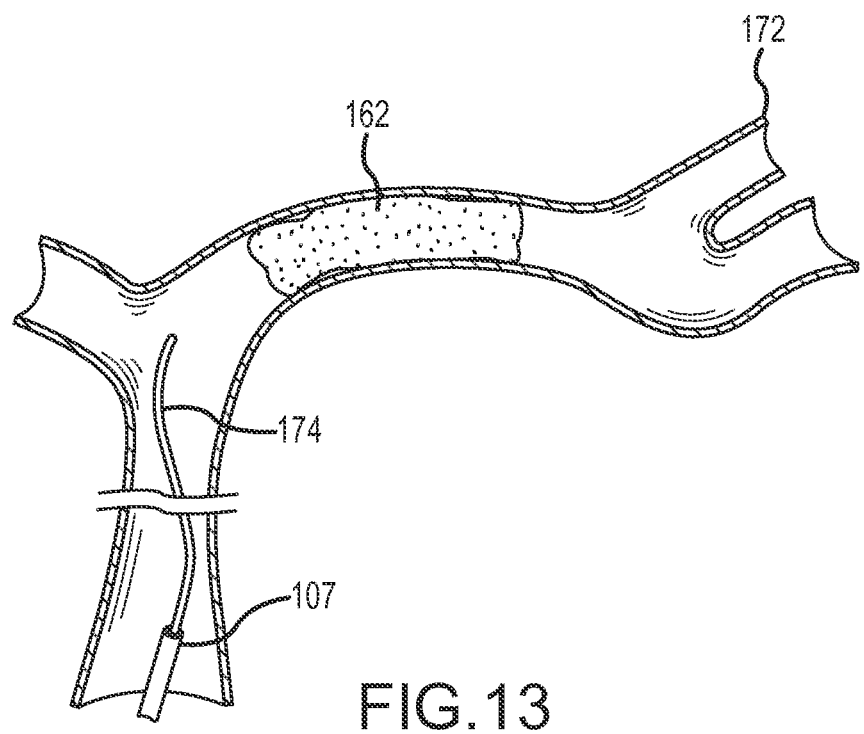
FIGS. 13-22 are cross-sectional views of a vessel and illustrate use of a device according to some embodiments.
Figure 14:
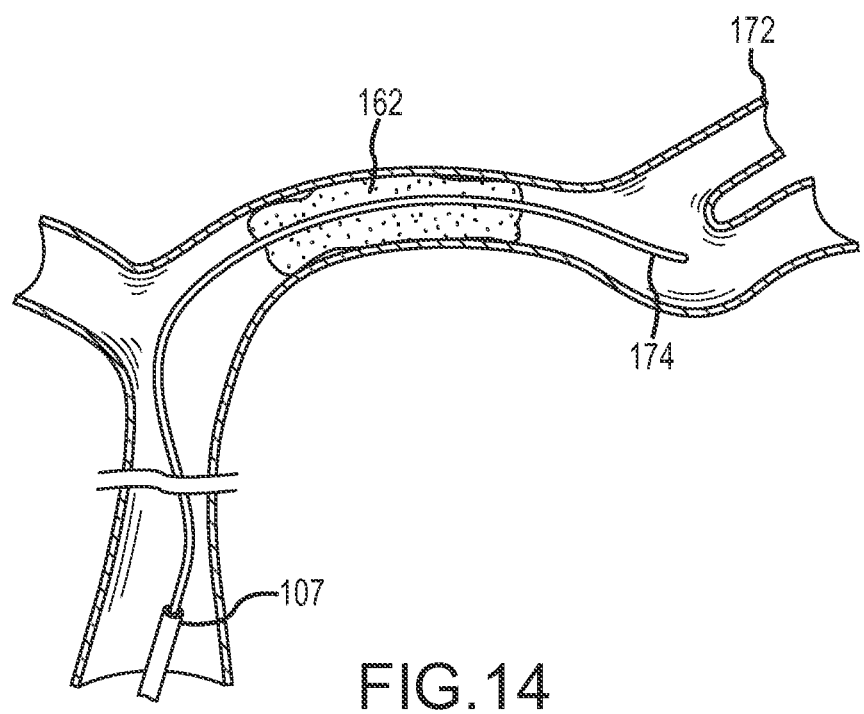
Figure 15:
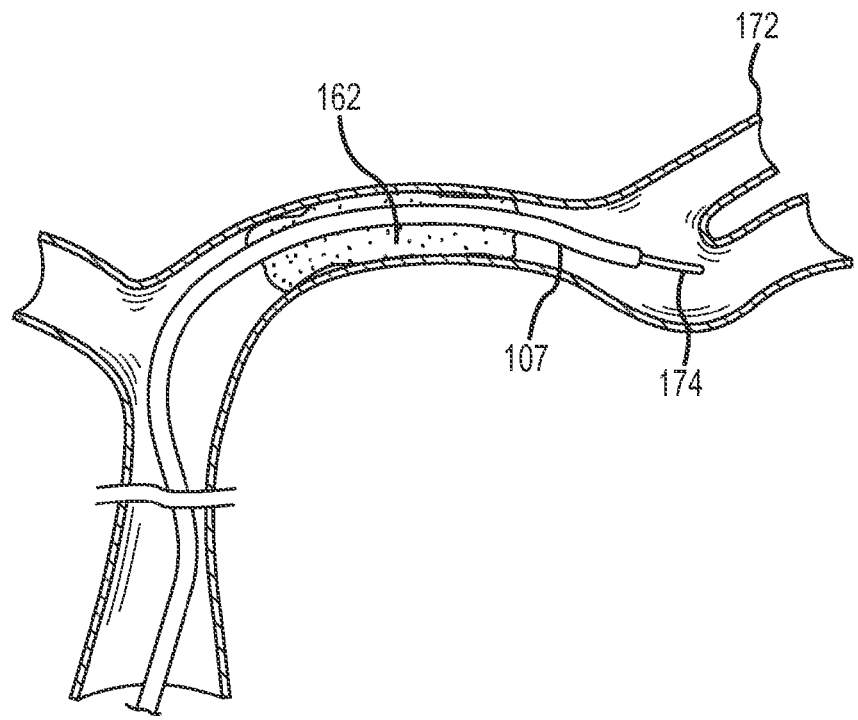

A technique for engaging and removing a thrombus 162 and restricting downstream travel of secondary emboli during thrombus retrieval will now be discussed with reference to FIGS. 13-22. This technique can be performed with any of the embodiments of the medical device 100 and expandable member 102 disclosed herein, including any of the expandable members 102 of FIG. 2, 8, 9 or 10. Referring to FIG. 13, the medical device 100 may be inserted into an anatomical vessel 172 by first inserting a guide wire 174 into the anatomical vessel 172. The guide wire 174 is advanced through a guide catheter 164, which optionally includes a balloon near the guide catheter's distal end, and a catheter 107 to the treatment site, adjacent the thrombus 162. Referring to FIG. 14, the guide wire 174 is advanced distally through the thrombus 162. Once in position, the catheter 107 is advanced over the guide wire 174, through a distal end of the guide catheter, into the anatomical vessel 172. Referring to FIG. 15, the catheter 107 is advanced distally through the thrombus 162. The guide wire 174 is then withdrawn proximally.

Figure 16:
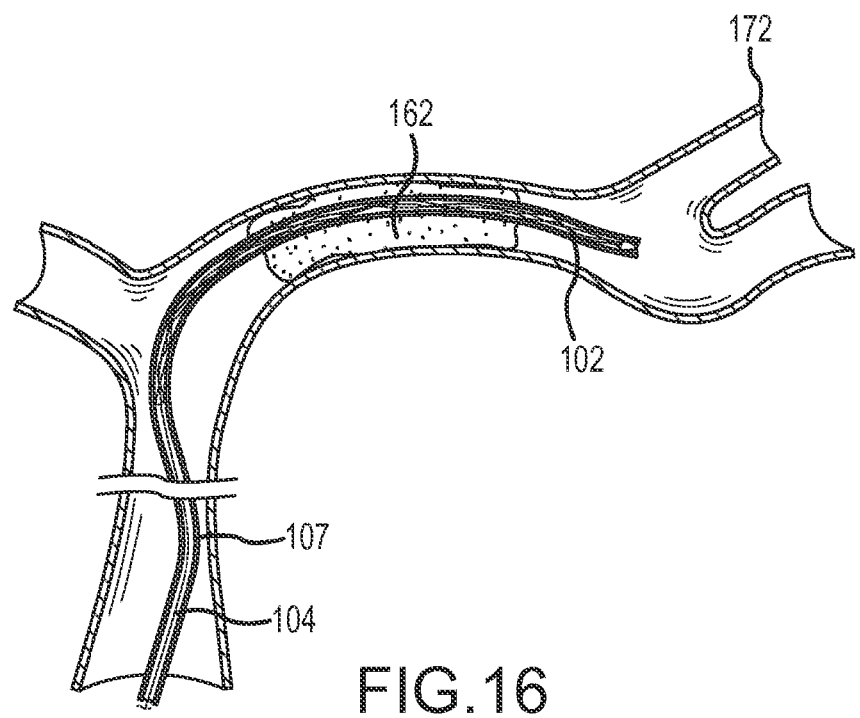

Referring to FIG. 16, the medical device 100 is advanced through the catheter 107 such that the distal portion 120 of the medical device 100 is disposed distal of the thrombus 162 in the anatomical vessel 172. The medical device 100 is advanced through the catheter 107 by the manipulation member 104 coupled to the proximal end of the expandable member 102. The catheter 107 compresses the expandable member 102 and thus, maintains the expandable member 102 in a compressed, volume-reduced configuration as the expandable member 102 is advanced to the treatment site.

Figure 17:
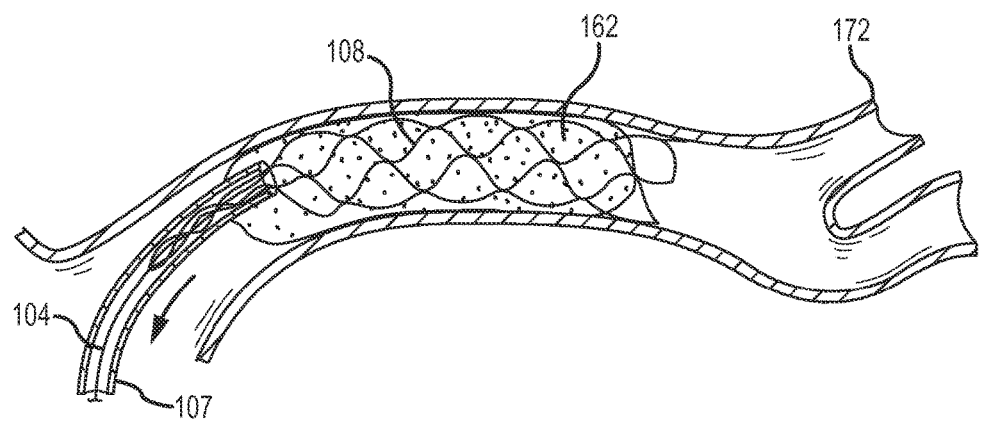
Figure 18:
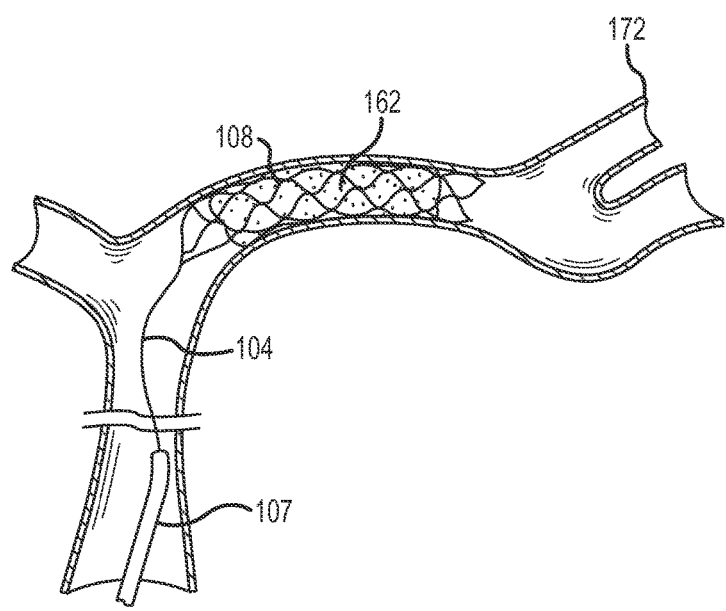

Referring to FIGS. 17 and 18, the catheter 107 is withdrawn proximally relative to the expandable member 102 to expose the expandable member 102. If the expandable member is self-expanding, retraction of the catheter 107 can permit the expandable member 102 to expand. The frame 108 expands against a length of the thrombus 162 and engages the thrombus 162. As discussed above, the frame 108 is designed to engage and remove thrombi that are both generally soft, or malleable, or generally hard, or callous. A period of time can be allowed to pass to allow blood to reperfuse the downstream area, the expandable member 102 to penetrate the thrombus 162, or both.

Figure 19:
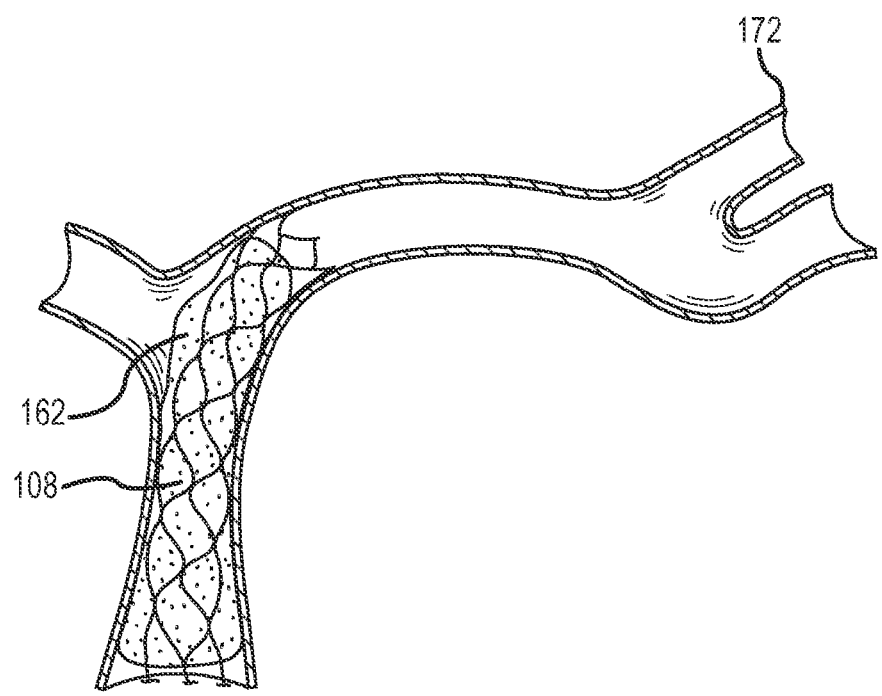
Figure 20:
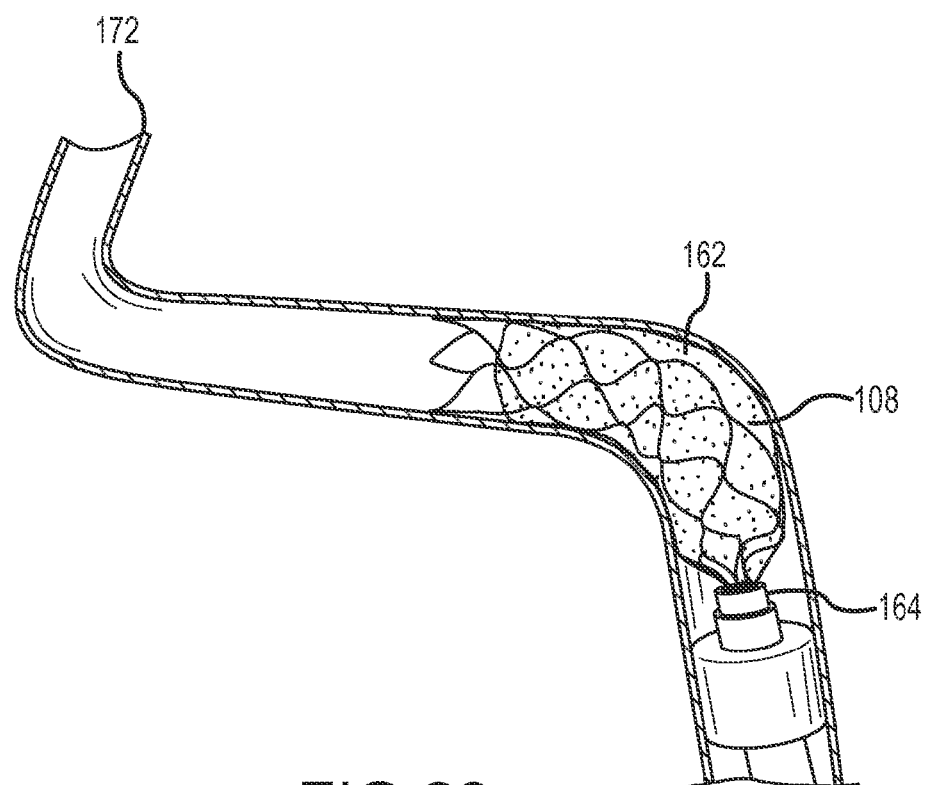

Referring to FIGS. 19 and 20, the expandable member 102 is withdrawn proximally, along with the thrombus 162. Applying a proximally directed force to a proximal end of the frame 108 can collapse a distal end of the frame 108, prior to withdrawal of the intervention member into the guide catheter 164. The distal end of the frame 108 can collapse to at least substantially the same extent, and optionally more than, a portion of the frame proximal of the distal end as discussed above.

Figure 21:
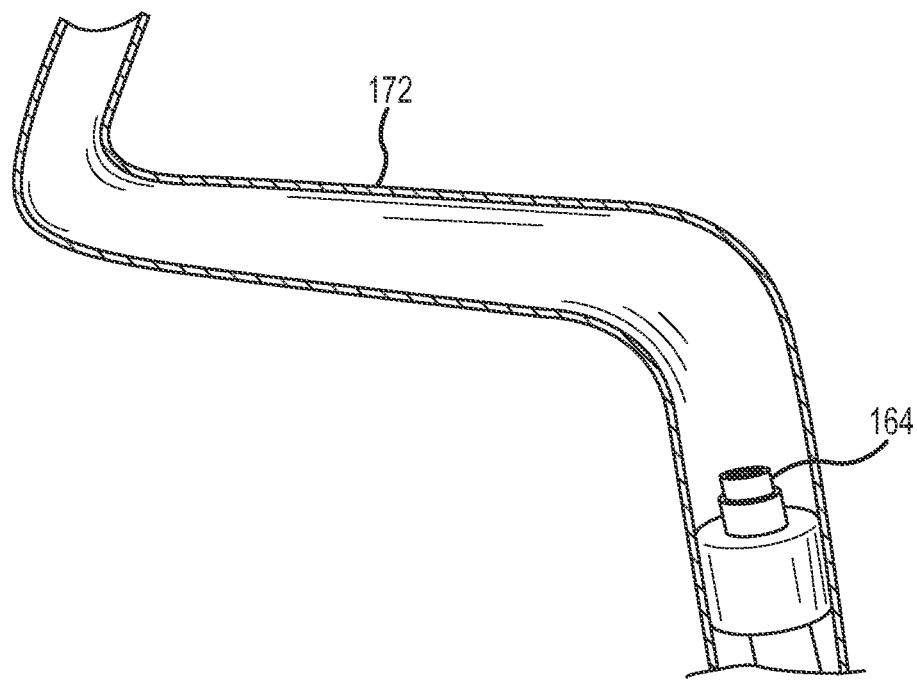

Referring to FIGS. 12, 20, and 21, in embodiments wherein the guide catheter 164 comprises a balloon 168, the balloon optionally can be inflated to occlude flow during retraction of the thrombus 162 toward the guide catheter. In some embodiments, an aspiration syringe 170 can be attached to the guide catheter 164, and aspiration can be applied to aid thrombus retrieval.

Figure 22:
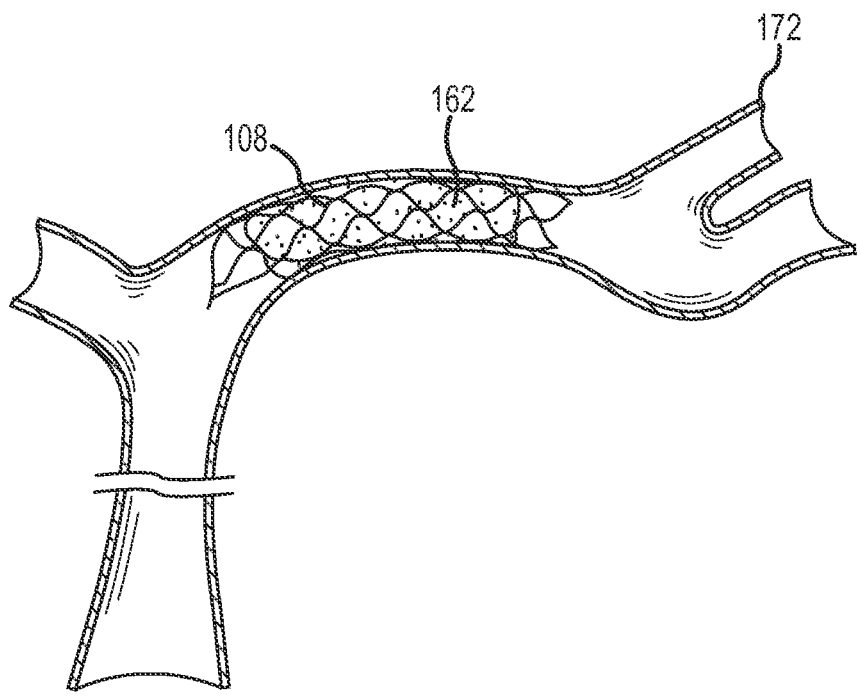

Referring to FIG. 21, the expandable member 102 is withdrawn proximally to the guide catheter 164. The guide catheter 164 causes the frame 108 to collapse, with the thrombus 162 engaged therein. The thrombus 162 is thus retrieved and removed from the anatomical vessel 172. Referring to FIG. 22, if retrieval of the expandable member 102 is determined to be undesirable, e.g., to avoid damaging the vessel 172, and the expandable member 102 is detachably connected to the manipulation member 104, the expandable member can be detached from the manipulation member 104 and can remain in the vessel 172.

Additionally, while the expandable member 102 described above has been described in the context of use during a blood flow restoration procedure, the expandable member 102 can also, or alternatively, be used as an implantable member (e.g. stent). For example, the expandable member 102 can be released through the connection 106 at a stenosis, aneurysm, or other appropriate location in a vessel. The expandable member 102 can expand and engage a vessel wall so as to hold the vessel wall open and/or act as an occluding member. While the filament thicknesses, widths, cell sizes, and forces described above can be optimized for an expandable member 102 for flow restoration, these values can also be optimized for an expandable member 102 for use as an implantable member. In some embodiments the same values can be used for both flow restoration and use as an implantable member.

Further details regarding expandable members, the manufacture of expandable members, and use of expandable members are disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. patent application Ser. No. 13/834,945, entitled Connection of an Endovascular Intervention Device to a Manipulation Member, filed on Mar. 15, 2013, published as U.S. Patent Application Publication No. 2014/0194919 on Jul. 10, 2014; and U.S. patent application Ser. No. 13/835,130, entitled Connection of a Manipulation Member, Including a Bend without Substantial Surface Cracks, to an Endovascular Intervention Device, filed on Mar. 15, 2013, published as U.S. Patent Application Publication No. 2014/0194911 on Jul. 10, 2014; the entirety of each of which is hereby incorporated by reference herein.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medical device configured to perform an endovascular therapy, the device comprising:
    an elongate manipulation member comprising a distal end portion; and
    an intervention member comprising a proximal end portion and a mesh, the proximal end portion being coupled with the distal end portion of the elongate manipulation member, the mesh having a proximal mesh end, a distal mesh end, and a mesh length from the proximal end to the distal end, the mesh having a plurality of cells and being compressible to a collapsed configuration for delivery to an endovascular treatment site through a catheter and being self-expandable from the collapsed configuration to an expanded configuration, and wherein at least a portion of the mesh, from a first location to a second location along the mesh, is configured such that an amount of cell deformation in response to longitudinally directed tensile forces decreases by less than 5% or increases in a distal direction along the portion of the mesh, the first and second locations being longitudinally separated by a distance that is more than half of the mesh length;
    wherein the mesh is generally cylindrical in the absence of external forces;
    wherein, in a longitudinal row of at least three cells, each cell includes first and second struts (i) bounding a proximal portion of the cell and (ii) diverging in a distal direction;
    wherein, in the longitudinal row, each cell distally adjacent to another cell has a larger proximal inscribed strut angle between the first and second struts than has the another cell; and
    wherein the first struts of all cells in the longitudinal row of at least three cells have substantially equal lengths.

2. The medical device of claim 1, wherein the portion of the mesh, from the first location to the second location along the mesh, is configured such that the amount of cell deformation in response to longitudinally directed tensile forces does not decrease in a distal direction along the portion of the mesh.

3. The medical device of claim 1, wherein the portion of the mesh, from the first location to the second location along the mesh, is configured such that the amount of cell deformation in response to longitudinally directed tensile forces increases in a distal direction along the portion of the mesh.

4. The medical device of claim 1, wherein the first and second locations are longitudinally separated by a distance that is at least two thirds of the mesh length.

5. The medical device of claim 1, wherein the first and second locations are longitudinally separated by a distance that is at least three quarters of the mesh length.

6. The medical device of claim 1, wherein the first and second locations are longitudinally separated by a distance that is at least 90% of the mesh length.

7. The medical device of claim 1, wherein, in the longitudinal row, each cell distally adjacent to another cell has a larger interior bounded area than has the another cell, and
    wherein each cell distally adjacent to another cell in the longitudinal row has a larger maximum cell width than has the another cell.

8. A medical device configured to perform an endovascular therapy, the device comprising:
    an elongate manipulation member comprising a distal end portion; and
    an intervention member comprising a proximal end portion and a plurality of cells forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration, and wherein, from a first location to a second location along the mesh, each cell distally adjacent to another cell, in a longitudinal row of cells, has a larger interior bounded area than has the another cell, the first and second locations being longitudinally separated by a distance that is more than half of the mesh length;
    wherein the mesh is generally cylindrical in the absence of external forces;
    wherein each of at least three consecutive cells in the longitudinal row includes first and second struts (i) bounding a proximal portion of the cell and (ii) diverging in a distal direction; and
    wherein, in the longitudinal row, each cell distally adjacent to another cell has a larger proximal inscribed strut angle between the first and second struts than has the another cell.

9. The medical device of claim 8, wherein the first and second locations are longitudinally separated by a distance that is at least two thirds of the mesh length.

10. The medical device of claim 8, wherein the first and second locations are longitudinally separated by a distance that is at least three quarters of the mesh length.

11. The medical device of claim 8, wherein the first and second locations are longitudinally separated by a distance that is at least 90% of the mesh length.

12. The medical device of claim 8, wherein the first location is at the proximal mesh end.

13. The medical device of claim 8, wherein the first location is distal to a proximal-most cell.

14. The medical device of claim 8, wherein the second location is at the distal mesh end.

15. The medical device of claim 8, wherein the elongate manipulation member has a length between a proximal end and the distal end portion that is sufficient to permit manipulation of the intervention member within the cerebral vasculature of a patient's body from a location outside the body.

16. The medical device of claim 8, wherein the mesh is formed by laser cutting one of a tube or a sheet.

17. The medical device of claim 8, wherein the mesh forms a generally tubular structure.

18. The medical device of claim 8, wherein the mesh further comprises a first lateral edge extending between the proximal mesh end and the distal mesh end, and a second lateral edge opposite the first lateral edge, the second lateral edge extending between the proximal mesh end and the distal mesh end; wherein the first and second lateral edges are overlapped in a coiled configuration about a longitudinal axis of the mesh when the mesh is in the collapsed configuration.

19. The medical device of claim 8, wherein the mesh has an open proximal end and an open distal end.

20. The medical device of claim 8, wherein the first struts of all cells in the longitudinal row of at least three cells have substantially equal lengths, and
wherein each cell distally adjacent to another cell in the longitudinal row has a larger maximum cell width than has the another cell.

21. A medical device configured to perform an endovascular therapy, the device comprising:
an elongate manipulation member comprising a distal end portion; and
an intervention member comprising a proximal end portion and a plurality of cells forming a mesh, the proximal end portion being coupled with the distal end portion of the elongate manipulation member, the mesh having a proximal mesh end, a distal mesh end, and a mesh length from the proximal end to the distal end, the mesh being compressible to a collapsed configuration for delivery to an endovascular treatment site through a catheter and being self-expandable from the collapsed configuration to an expanded configuration,
wherein, in a longitudinal row of at least three cells, each cell includes first and second struts (i) bounding a proximal portion of the cell and (ii) diverging in a distal direction, and wherein, in the longitudinal row, each cell distally adjacent to another cell has a larger proximal inscribed strut angle between the first and second struts, than has the another cell;
wherein the mesh is generally cylindrical in the absence of external forces; and
wherein each cell distally adjacent to another cell in the longitudinal row has a larger maximum cell width than has the another cell.

22. The medical device of claim 21, wherein each of the first and second struts comprises a straight portion and a curved portion, and the inscribed strut angle is measured between the straight portions of the first and second struts.

23. The medical device of claim 21, wherein the inscribed strut angle is measured between straight reference lines that join strut intersection points at each end of the first and second struts.

24. The medical device of claim 21, wherein the longitudinal row extends from a first location to a second location along the mesh, the first and second locations being longitudinally separated by a distance that is more than half of the mesh length.

25. The medical device of claim 21, wherein, for each cell, the first strut has a length equal to that of the second strut.

26. The medical device of claim 24, wherein the first struts of all cells between the first and second locations have substantially equal lengths.

27. The medical device of claim 24, wherein the first and second locations are longitudinally separated by a distance that is at least two thirds of the mesh length.

28. The medical device of claim 24, wherein the first and second locations are longitudinally separated by a distance that is at least three quarters of the mesh length.

29. The medical device of claim 24, wherein the first and second locations are longitudinally separated by a distance that is at least 90% of the mesh length.

30. The medical device of claim 21, wherein each cell comprises first and second struts (i) bounding a proximal portion of the cell and (ii) diverging in a distal direction, and third and fourth struts (i) bounding a distal portion of the cell and (ii) converging in a distal direction, the maximum cell width is measured from an intersection of the first strut and the third strut to an intersection of the second strut with the fourth strut.

31. The medical device of claim 21, wherein the first struts of all cells in the longitudinal row of at least three cells have substantially equal lengths, and
wherein, in the longitudinal row, each cell distally adjacent to another cell has a larger interior bounded area than has the another cell.

\* \* \* \* \*